US012751448B2

(12) United States Patent
Basel et al.

(10) Patent No.: US 12,751,448 B2
(45) Date of Patent: Oct. 6, 2026

(54) METHODS OF TREATING CROP PLANTS

(71) Applicant: AGROFRESH, INC., Collegeville, PA (US)

(72) Inventors: Richard Martin Basel, Fostoria, OH (US); Jon Frederick Fobes, Lower Gwynedd, PA (US); Edward Charles Kostansek, Buckingham, PA (US); Robert Lynn Oakes, Doylestown, PA (US); Arden Nathan Reed, Wenatchee, WA (US); Todd Bryan Edgington, Research Triangle Park, NC (US); Timothy Malefyt, Stroudsburg, PA (US); Al Green, Des Moines, IA (US)

(73) Assignee: AGROFRESH INC., Philadelphia, PA (US)

( * ) Notice: Subject to any disclaimer, the term of this patent is extended or adjusted under 35 U.S.C. 154(b) by 1183 days.

(21) Appl. No.: 17/216,760

(22) Filed: Mar. 30, 2021

(65) Prior Publication Data

US 2021/0219546 A1 Jul. 22, 2021

Related U.S. Application Data

(63) Continuation of application No. 14/707,958, filed on May 8, 2015, now abandoned.

(51) Int. Cl.

| | |
|---|---|
| ***A01N 27/00*** | (2006.01) |
| ***A01G 7/06*** | (2006.01) |
| ***A01H 3/04*** | (2006.01) |
| ***A01N 25/02*** | (2006.01) |

(52) U.S. Cl.
CPC ............... *A01N 27/00* (2013.01); *A01G 7/06* (2013.01); *A01H 3/04* (2013.01); *A01N 25/02* (2013.01)

(58) Field of Classification Search
CPC .......... A01N 27/00; A01N 25/02; A01H 3/04; A01G 7/06
See application file for complete search history.

(56) References Cited

U.S. PATENT DOCUMENTS

| | | | | |
|---|---|---|---|---|
| 5,100,462 A ‡ | 3/1992 | Sisler | A01N 3/02 | 504/115 |
| 5,228,899 A ‡ | 7/1993 | Itoh | A01N 37/36 | 504/114 |
| 5,292,937 A ‡ | 3/1994 | Manning | A01N 37/04 | 504/315 |
| 5,518,988 A ‡ | 5/1996 | Sisler | A01N 3/02 | 504/114 |
| 5,575,988 A ‡ | 11/1996 | Knowles, Jr. | A61K 8/42 | 424/59 |
| 5,834,403 A ‡ | 11/1998 | Callan | A01N 37/36 | 504/319 |
| 6,017,849 A ‡ | 1/2000 | Daly | A01N 43/90 | 504/114 |
| 6,194,350 B1 ‡ | 2/2001 | Sisler | A01N 3/02 | 504/114 |
| 6,357,207 B1 ‡ | 3/2002 | Weder | B65B 25/023 | 53/412 |
| 6,365,549 B2 ‡ | 4/2002 | Sisler | A01N 3/02 | 504/114 |
| 6,426,319 B1 ‡ | 7/2002 | Kostansek | A01N 3/02 | 504/357 |
| 6,548,448 B2 ‡ | 4/2003 | Kostansek | A01N 3/00 | 206/423 |
| 6,762,153 B2 ‡ | 7/2004 | Kostansek | A01N 3/02 | 504/357 |
| 6,887,900 B2 ‡ | 5/2005 | Williams | A01N 37/02 | 514/549 |
| 6,897,185 B1 ‡ | 5/2005 | Chang | A01N 27/00 | 504/357 |
| 6,953,540 B2 ‡ | 10/2005 | Chong | B01J 13/02 | 264/4.1 |
| 7,041,625 B2 ‡ | 5/2006 | Jacobson | A01N 27/00 | 504/193 |
| 2001/0019995 A1 ‡ | 9/2001 | Sisler | A01N 33/04 | 504/114 |
| 2002/0053514 A1 ‡ | 5/2002 | Locascio | B32B 3/20 | 204/454 |
| 2004/0029736 A1 ‡ | 2/2004 | Hansen | A01N 27/00 | 504/319 |

(Continued)

FOREIGN PATENT DOCUMENTS

| | | |
|---|---|---|
| AU | 2005242218 | 8/2006 |
| EP | 1410712 ‡ | 4/2004 |

(Continued)

OTHER PUBLICATIONS

Marcellis, L F M , et al , "Flower and fruit abortion in sweet pepper in relation to source and sink strength," Journal of Experimental Biology, 2004, No. 406, pp. 2261-2268.‡

Prange, R K , et al , "1-Methylcyclopropen The magic bullet' for Horticultural Products" Chronica Horticulturae, 2003, pp. 11-14, vol. 43.‡

Jones, et al , "Role of Ethylene and 1-MCP in Flower Development and Petal Abscission in Zonal Geraniums," Horticultural Science, v 36, No. 7, Previously Presented 1305-1309, 2001.‡

Sisler, E C , et al , "Inhibition of ethylene response by 1-methylcyclopropene and 3-methylcyclopropene," Plant Growth Regulation, vol. 27, pp. 105-111, 1999 Abstract Only.‡

Do, et al , "The role of ethylene during reproductive development in wheat (*Triticum aestivum*) under ," Am Soc Of Plant Biologists Symposium, Seattle, WA, (2005).‡

(Continued)

*Primary Examiner* — Ali Soroush
*Assistant Examiner* — Andriae M Holt
(74) *Attorney, Agent, or Firm* — Barnes & Thornburg LLP

(57) ABSTRACT

A method of treating dicot seedlings comprises contacting dicot seedlings with a composition comprising at least one cyclopropene one or more times prior to transplanting the dicot seedlings. A method of treating crop plants comprises contacting crop plants one or more times with a composition comprising at least one cyclopropene while the crop plants are at a specific development stage, such as reproductive stage.

14 Claims, No Drawings

(56) References Cited

U.S. PATENT DOCUMENTS

| | | | | |
|---|---|---|---|---|
| 2004/0072694 | A1‡ | 4/2004 | Jacobson | A01N 27/00 504/326 |
| 2004/0192554 | A1‡ | 9/2004 | Kashimura | A01N 27/00 504/357 |
| 2005/0065033 | A1‡ | 3/2005 | Jacobson | C07C 13/04 504/343 |
| 2005/0261131 | A1‡ | 11/2005 | Basel | A01N 27/00 504/353 |
| 2005/0261132 | A1‡ | 11/2005 | Kostansek | A01N 3/00 504/353 |
| 2005/0288189 | A1‡ | 12/2005 | Jacobson | A01N 35/10 504/343 |
| 2006/0160704 | A1‡ | 7/2006 | Basel | A01N 57/20 504/136 |
| 2007/0093389 | A1‡ | 4/2007 | Rademacher | A01N 37/50 504/116.1 |
| 2007/0117720 | A1‡ | 5/2007 | Jacobson | A01N 27/00 504/118 |
| 2007/0149401 | A1‡ | 6/2007 | Haskell | A01N 37/46 504/103 |
| 2007/0199242 | A1‡ | 8/2007 | Hansen | A01N 27/00 47/89 |
| 2007/0265166 | A1‡ | 11/2007 | Bardella | A01N 27/00 504/357 |
| 2007/0265167 | A1‡ | 11/2007 | Edgington | A01N 27/00 504/357 |
| 2013/0298290 | A1‡ | 11/2013 | Haas | A01N 43/653 800/298 |

FOREIGN PATENT DOCUMENTS

| | | | |
|---|---|---|---|
| EP | 1609359 | ‡ | 12/2005 |
| EP | 1680960 | ‡ | 7/2006 |
| EP | 1856976 | ‡ | 11/2007 |
| JP | 10-501231 | ‡ | 2/1998 |
| JP | 3-169857 | ‡ | 12/1998 |
| JP | 2000-023675 | ‡ | 1/2000 |
| JP | 2003-201201 | ‡ | 7/2003 |
| JP | 2005-145984 | ‡ | 6/2005 |
| JP | 2007-308491 | ‡ | 11/2007 |
| NZ | 519036 | ‡ | 2/2004 |
| RU | 2267477 | ‡ | 1/2006 |
| WO | WO-95/33377 | ‡ | 12/1995 |
| WO | WO-00/10386 | ‡ | 3/2000 |
| WO | 2001/037663 | | 5/2001 |
| WO | WO-2004/014137 | ‡ | 2/2004 |
| WO | WO-2005044002 | ‡ | 5/2005 |
| WO | WO-2007001919 | ‡ | 1/2007 |
| WO | WO-2007096833 | ‡ | 8/2007 |
| WO | WO-2007104660 | ‡ | 9/2007 |
| WO | WO-2014059209 | ‡ | 4/2014 |

OTHER PUBLICATIONS

Sisler, E C , et al , "Inhibitors of ethylene responses in plants at the receptor level Recent developments" Physiologica Plantarum, 1997, pp. 577-582, vol. 100.‡

Dekazos, E D , "Effect of Aminoethoxyvinyl Glycine on Bloom Delay Fruit Quality and Chemical pruning of Apple Malus-Domestica Trees," Hortscience, vol. 16, No. 3 SECT 2, 1981, p. 455, XP002689050, ISSN 0018-5345.‡

Sisler, E C , et al , "Compounds interacting with the ethylene receptor in plants," Plant Biology, Wiley-Blackwell Publishing Ltd, GB, DE, NL, vol. 5, No. 5, Sep. 1, 2003 (Sep. 1, 2003), pp. 473-480, XP002502595, ISSN 1435-8603, DOI 10 1055/S-2003-44782.‡

Greene, Duane W , et al , "Effect of aminoethoxyvinylglycine (AVG) on preharvest drop, fruit quality, and maturation of 'McIntosh' Apples II Effect of timeing and concentration relationships and spray volume," Hortscience, vol. 39, No. 5, Aug. 2004 (Aug. 2004), p. 1036, XP002689049, ISSN 0018-5345.‡

Search Report for EP07251871, Jan. 10, 2013.‡

Fan, X, Development of Apple of Superficial Scald, Soft Scald, Core Flush, and Greasiness is Reduced by MCP, 1999, Journal of Agriculture and Food Chemistry, vol. 47, pp. 3063-3068.‡

Byers, R E , et al , "Ethylene Inhibitors Delay Fruit Drop, Maturity, and Increase Fruit Size of 'Arlet' Apples," Hortscience, Dec. 2005, pp. 2061-2065, vol. 40.‡

Byers, Re, et al , "Pre Harvest Fruit Drop, Harvest Quality, and Cold Storage of 'Golden Delicious' and 'Rome' Apples," Proceedings of the Plant Growth Regulation Society of America, v 27, pp. 175-180, 2000.‡

Blankenship, et al , "1-Methylcyclopropene a review," Postharvest Biology and Technology, 2003, pp. 1-25, vol. 28.‡

Kubota, C., Application of 1-MCP for Quality Preservation of Tomato (*Lycopersicon esculentum*) Seedlings during Long-distance Transporation, Jul. 2006, HortScience, vol. 41, Issue 4, pp. 967 and 976.‡

Sosnoskie, L., Breaking Bindweed: Deciphering the complex interactions among weed, water, herbicide, and crop to improve Convolvulous arvensis control in processing tomato, 2015, California Tomato Research Institute, 2015 Summary Project Report, 3 pages.‡

Byers, R. E., et al., "Pre Harvest Fruit Drop, Harvest Quality, and Cold Storage of 'Golden Delicious' and 'Rome' Apples," Proceedings of the Plant Grmvth Regulation Society of America, v. 27, pp. 175-180, 2000.

Sisler, E.G., et al., "Compounds interacting with the ethylene receptor in plants," Plant Biology, Wiley-Blackwell Publishing Ltd, GB, DE, NL, vol. 5, No. 5, Sep. 1, 2003 {Sep. 1, 2003), pp. 473-480, XP002502595, ISSN: 1435-8603, DOI: 10.1055/S-2003-44782.

Sisler, E.G., et al., "Inhibition of ethylene response by 1-methylcyclopropene and 3-methylcyclopropene," Plant Growth Regulation, vol. 27, pp. 105-111, 1999. Abstract Only.

Sisler, E.G., et al., "Inhibitors of ethylene responses in plants at the receptor level: Recent developoments" Physiologica Plantarum, 1997, pp. 577-582, vol. 100.

Kubota, C., Application of 1-MCP for Quality Preservation of Tomato (*Lycopersicon esculentum*) Seedlings during Long-distance Transportation, Jul. 2006, HortScience, vol. 41, Issue 4, pp. 967 and 976.

International Search Report and Written Opinion, International Application No. PCT/US16/031445, mailed Aug. 19, 2016.

European Search Report issued on Jan. 10, 2013, in connection with EP07251871.

Sisler et al., "1-substituted cyclopropenes: Effective Blocking Agents for Ethylene Action in Plants," Plant Growth Regulation 40: 223-228, 2003.

Porat et al., "1-Methylcyclopropene inhibits ethylene action in cut phlox flowers," Postharvest Biol & Tech, 6(3-4), 313-319, 1995.

Kawakami et al., "Effect of 1-MCP on the Growth and Yield of Cotton," Summaries of Arkansas Cotton Research, AAES Research Series, p. 58-66, 2006.

‡ imported from a related application

METHODS OF TREATING CROP PLANTS

CROSS-REFERENCE TO RELATED APPLICATIONS

This application is a continuation of U.S. patent application Ser. No. 14/707,958 filed on May 8, 2015, the disclosure of which is hereby incorporated herein in its entirety by this reference.

TECHNICAL FIELD

This disclosure relates to methods of treating crop plants and to methods of treating dicot seedlings to improve quality, yield and/or environmental stress tolerance of crop plants.

BACKGROUND

Plants are often treated with chemical compositions to control attack from pests (e.g., insects) and/or vegetation (e.g., weeds or fungi), as well as to promote plant growth and/or yield. It is also desirable to protect plants from abiotic environmental stress (e.g., heat, cold, high wind, salinity, drought, or flood) that may adversely affect their growth and productivity. Further, plants may suffer and/or die from transplant shock when they are transplanted from one location to another location. When plants are under such environmental stress, significant losses in quality and yield are commonly observed.

L. Pozo et al. report that the citrus trees treated with liquid solutions containing an abscission agent and 1-methyl cyclopropene (1-MCP) showed low fruit detachment force and low levels of leaf abscission. L. Pozo et al., *Differential Effects of* 1-*Methylcyclopropene on Citrus Leaf and Mature Fruit Abscission*, J. Amer. Soc. Hort. Sci., 2004, 129(4), pp. 473-478.

U.S. Patent Publication No. 2006/0160704 discloses methods of increasing crop yield of non-citrus plants by contacting non-citrus plants with a composition comprising cyclopropene and a composition comprising a plant growth regulator that is not a cyclopropene.

U.S. Patent Publication No. 2010/0304975 discloses methods for increasing the abiotic environmental stress tolerance of plants by foliar field spraying plants with a composition comprising a xyloglucan derivative between 1 hour and 72 hours before the abiotic environmental stress arrives.

U.S. Patent Publication No. 2013/0298290 discloses methods of increasing the abiotic environmental stress tolerance of plants by adding cyclopropene in the plant irrigation water.

U.S. Pat. No. 8,119,855 discloses methods for conferring tolerance to abiotic stress to plants by transforming plants with a nucleotide sequence encoding an RKS protein, especially an RKS subgroup II protein (more specifically RKS1, RKS4 or truncated RKS4), or an RKS subgroup III (more preferably RKS12).

U.S. Pat. No. 8,889,949 discloses methods for increasing resistance of monocot plants against abiotic stress by transforming the monocot plants with a recombinant plasmid containing a fused gene (TPSP) of trehalose-6 phosphate synthetase (TPS) gene and trehalose-6-phosphate phosphatase (TPP) gene to express the TPSP gene, while maintaining normal plant growth and development characteristics.

SUMMARY OF THE DISCLOSURE

In one aspect for present disclosure, a methods of treating crop plants comprises contacting crop plants one or more times with a composition comprising at least one cyclopropene, while the crop plants are at a particular development stage appropriate for such crop plants.

In other aspect for present disclosure, a methods of treating crop plants comprises contacting crop plants one or more times with a composition comprising at least one cyclopropenes, while the crop plants are at one or more reproductive stage.

In yet other aspect for present disclosure, a method of treating crop plants or seedlings comprises contacting the crop plants or seedlings one or more times with a composition comprising at least one cyclopropenes, and transplanting the crop plants or seedlings from one location to another location.

In further aspect for present disclosure, a method of treating dicot seedlings comprises contacting dicot seedlings one or more times with a composition comprising at least one cyclopropenes from minutes to 7 days prior to transplanting the dicot seedlings.

DETAILED DESCRIPTION

As used herein, the term "seedling" or grammatical variations thereof means and includes a young plant sporophyte developing out of a plant embryo from a seed. Seedling development starts with germination of the seed, which is commonly performed in a controlled environment, e.g., greenhouse, hotbed, cold frame.

As used herein, the term "transplanting" or grammatical variations thereof means and includes moving a plant from one location and replanting it at another location.

As used herein, the term "abiotic stress" or grammatical variations thereof means and includes the impact of non-living factors on plants in a specific environment that is beyond its normal range of variation and results in a significant adverse effect on the performance of a plant population or the individual physiology of a plant. Example of abiotic stress may include, but are not limited to, heat, cold, high wind, salinity, drought, flood, osmotic stress, or salinity.

As used herein, the term "crop plants" or grammatical variations thereof means and includes plants that are grown for the purpose of removing one or more plant parts, when such parts are considered a useful product.

As used herein, the term "horticultural crops", "horticultural crop plants" or grammatical variations thereof means and includes agricultural products that are not agronomic crops and are not forestry products. Agronomic crops are herbaceous field crops, including grains, forages, oilseeds, and fiber crops. Forestry products are forest trees and forest products. Horticultural crop plants are usually relatively intensively managed plants that are cultivated for food or for aesthetic purposes. Some typical horticultural crops are fruits, vegetables, spices, herbs, and plants grown for ornamental use.

As used herein, the term "harvesting" or grammatical variations thereof means and includes an act of removing useful plant parts from crop plants.

As used herein, the term "cyclopropene" means and includes any compound with the following formula

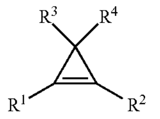

where each $R^1$, $R^2$, $R^3$ and $R^4$ is independently selected from the group consisting of H and a chemical group of the formula $$-(L)_n-Z$$

wherein:

n is an integer from 0 to 12;

each L is independently selected from the group consisting of D1, D2, E, and J;

where D1 is of the formula

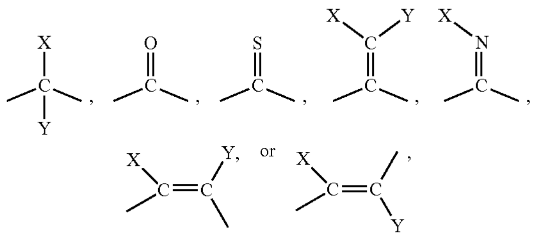

where D2 is of the formula

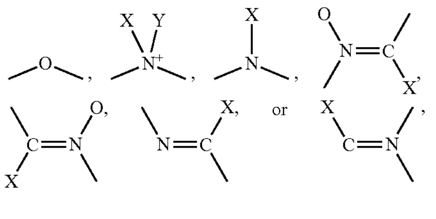

where E is of the formula

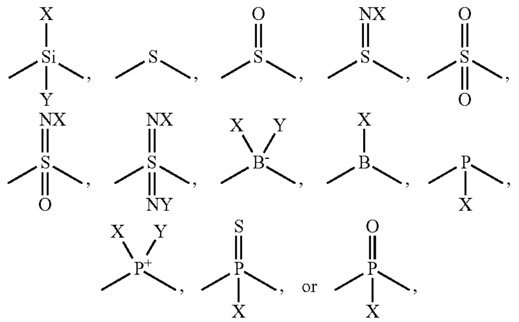

where J is of the formula:

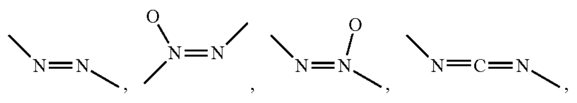

-continued

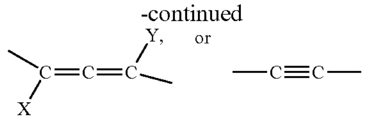

where each X and Y is independently a chemical group of the formula $$-(L)_m-Z,$$

m is an integer from 0 to 8, and no more than two D2 or E groups are adjacent to each other and no J groups are adjacent to each other; and each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system, where the total number of heteroatoms in $-(L)_n-Z$ is from 0 to 6, and where the total number of non-hydrogen atoms in the compound is 50 or less.

For the purposes of this disclosure, in the structural representations of the various L groups, each open bond indicates a bond to another L group, a Z group, or the cyclopropene moiety. For example, the structural representation

indicates an oxygen atom with bonds to two other atoms; it does not represent a dimethyl ether moiety.

Among embodiments in which at least one of $R^1$, $R^2$, $R^3$ and $R^4$ is not hydrogen and has more than one L group, the L groups within that particular $R^1$, $R^2$, $R^3$ or $R^4$ group may be the same as the other L groups within that same $R^1$, $R^2$, $R^3$ or $R^4$ group, or any number of L groups within that particular $R^1$, $R^2$, $R^3$ or $R^4$ group may be different from the other L groups within that same $R^1$, $R^2$, $R^3$ or $R^4$ group.

Among embodiments in which at least one of $R^1$, $R^2$, $R^3$ and $R^4$ contains more than one Z group, the Z groups within that $R^1$, $R^2$, $R^3$ or $R^4$ group may be the same as the other Z groups within that $R^1$, $R^2$, $R^3$ or $R^4$ group, or any number of Z groups within that $R^1$, $R^2$, $R^3$ or $R^4$ group may be different from the other Z groups within that $R^1$, $R^2$, $R^3$ or $R^4$ group.

$R^1$, $R^2$, $R^3$ and $R^4$ groups are independently selected from the suitable groups. $R^1$, $R^2$, $R^3$, and $R^4$ groups may be the same as each other, or any number of them may be different from the others. Examples of groups that are suitable for use as one or more of $R^1$, $R^2$, $R^3$ and $R^4$ may include, but are not limited to, aliphatic groups, cycloaliphatic groups, aliphatic-oxy groups, alkylphosphonato groups, alkylsulfonyl groups, cycloalkylsulfonyl groups, alkylamino groups, cycloalkylamino groups, alkylaminosulfonyl groups, alkylcarbonyl groups, heterocyclic groups, aryl groups, heteroaryl groups, halogens, silyl groups, other groups, and mixtures and combinations thereof. Groups that are suitable for use as one or more of $R^1$, $R^2$, $R^3$ and $R^4$ may be substituted or unsubstituted. Independently, groups that are suitable for use as one or more of $R^1$, $R^2$, $R^3$ and $R^4$ may be connected directly to the cyclopropene ring or may be connected to the cyclopropene ring through an intervening group such as, for example, a heteroatom-containing group.

Examples of aliphatic groups may include, but are not limited to, alkyl, alkenyl, and alkynyl groups. Suitable aliphatic groups may be substituted or unsubstituted. Some suitable substituted aliphatic groups may include, but are not limited to, acetylaminoalkenyl, acetylaminoalkyl, acetylaminoalkynyl, alkoxyalkoxyalkyl, alkoxy alkenyl, alkoxyalkyl, alkoxyalkynyl, alkoxycarbonylalkenyl, alkoxycarbonylalkyl, alkoxy carbonylalkynyl, alkylcarbonyloxyalkyl, alkyl(alkoxyimino)alkyl, carboxyalkenyl, carboxyalkyl, carboxyalkynyl, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylaminoalkyl, alkylsulfonylalkyl, alkylthioalkenyl, alkylthioalkyl, alkylthioalkynyl, haloalkylthioalkenyl, haloalkylthioalkyl, or haloalkylthioalkynyl.

Examples of aliphatic-oxy groups may include, but are not limited to, alkenoxy, alkoxy, alkynoxy, and alkoxycarbonyloxy. Examples of alkylphosphonato groups may include, but are not limited to, alkylphosphonato, dialkylphosphato, or dialkylthiophosphato. Non-limiting example of alkylamino groups may be dialkylamino or monalkylamino. Non-limiting example of alkylsulfonyl groups may be dialkylamino sulfonyl.

Examples of cycloaliphatic groups may include, but are not limited to, cycloalkenyl, cycloalkyl, and cycloalkynyl. Suitable cycloaliphatic groups may be substituted or unsubstituted. Among the suitable substituted cycloaliphatic groups are, for example, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, haloalkylthiocycloalkenyl, haloalkylthiocycloalkyl, or haloalkylthiocycloalkynyl.

Examples of heterocyclyl groups (i.e., non-aromatic cyclic groups with at least one heteroatom in the ring) may include, but are not limited to, substituted or unsubstituted cycloalkylsulfonyl groups or cycloalkylamino groups, such as, for example, dicycloalkylaminosulfonyl or dicycloalkylamino. Suitable substituted heterocyclyl groups may be substituted or unsubstituted. Among the suitable substituted heterocyclyl groups are, for example, alkenylheterocyclyl, alkylheterocyclyl, alkynylheterocyclyl, acetylaminoheterocyclyl, alkoxyalkoxyheterocyclyl, alkoxyheterocyclyl, alkoxycarbonylheterocyclyl, alkylcarbonyloxyheterocyclyl, carboxyheterocyclyl, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, or haloalkylthioheterocyclyl.

Examples of substituted and unsubstituted heterocyclyl groups that are connected to the cyclopropene compound through an intervening oxy group, amino group, carbonyl group, or sulfonyl group may include, but are not limited to, heterocyclylcarbonyl, diheterocyclylamino, or diheterocyclylaminosulfonyl.

Examples of substituted and unsubstituted aryl groups may include, but are not limited to, alkenylaryl, alkylaryl, alkynylaryl, acetylaminoaryl, aryloxy, alkoxyalkoxyaryl, alkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, and haloalkylthioaryl.

Examples of heteroaryl groups may include, but are not limited to, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarylsulfonylalkyl, alkylthioheteroaryl, or haloalkylthioheteroaryl.

Examples of substituted and unsubstituted heteroaryl groups that are connected to the cyclopropene compound through an intervening oxy group, amino group, carbonyl group, sulfonyl group, thioalkyl group, or aminosulfonyl group may include, but are not limited to, diheteroarylamino, heteroarylthioalkyl, or diheteroarylaminosulfonyl.

Further examples of suitable $R^1$, $R^2$, $R^3$ and $R^4$ groups may include, but are not limited to, hydrogen, fluoro, chloro, bromo, iodo, cyano, nitro, nitroso, azido, chlorato, bromato, iodato, isocyanato, isocyanido, isothiocyanato, pentafluorothio, acetoxy, carboethoxy, cyanato, nitrato, nitrito, perchlorato, allenyl, butylmercapto, diethyl phosphonato, dimethylphenylsilyl, isoquinolyl, mercapto, naphthyl, phenoxy, phenyl, piperidino, pyridyl, quinolyl, triethylsilyl, trimethylsilyl, or substituted analogs thereof.

As used herein, the chemical group G is a 3 to 14 membered ring system. Ring systems suitable as chemical group G may be substituted or unsubstituted. Further, they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, or fused. Among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated three-membered ring, such as, for example, a substituted or unsubstituted cyclopropane, cyclopropene, epoxide, or aziridine ring.

In some embodiments, G is a ring system that contains a four membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from chemical groups in the category X as defined herein below. Also suitable are embodiments in which G is a carbocyclic ring system.

Examples of suitable G groups may include, but are not limited to, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl) phenyl, 2-iodo-4-methylphenyl, pyridin-2-yl, pyridin-3-yl, pyridin-4-yl, pyrazinyl, pyrimidin-2-yl, pyrimidin-4-yl, pyrimidin-5-yl, pyridazinyl, triazol-1-yl, imidazol-1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl, 5-methyl-6-chromanyl, adamantyl, norbornyl, or their substituted analogs such as, for example: 3-butyl-pyridin-2-yl, 4-bromo-pyridin-2-yl, 5-carboethoxy-pyridin-2-yl, or 6-methoxyethoxy-pyridin-2-yl.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there are 1, 2, or 3 substituents. Independently, also among embodiments in which G is substituted phenyl are embodiments, for example, in which the substituents are independently selected from methyl, methoxy, and halo.

In some embodiments, one or more cyclopropenes are used in which one or more of $R^1$, $R^2$, $R^3$ and $R^4$ is hydrogen. In some embodiments, $R^1$ or $R^2$ or both $R^1$ and $R^2$ is hydrogen. Independently, in some embodiments, $R^3$ or $R^4$ or both $R^3$ and $R^4$ is hydrogen. In some embodiments, $R^2$, $R^3$, and $R^4$ are hydrogen.

In some embodiments, one or more of $R^1$, $R^2$, $R^3$ and $R^4$ is a structure that has no double bond. Independently, in some embodiments, one or more of $R^1$, $R^2$, $R^3$, and $R^4$ is a structure that has no triple bond. Independently, in some embodiments, one or more of $R^1$, $R^2$, $R^3$ and $R^4$ is a structure that has no halogen atom substituent. Independently, in some embodiments, one or more of $R^1$, $R^2$, $R^3$ and $R^4$ is a structure that has no substituent that is ionic. Independently, in some embodiments, one or more of $R^1$, $R^2$, $R^3$ and $R^4$ is a structure that is not capable of generating oxygen compounds.

In some embodiments of the disclosure, one or more of $R^1$, $R^2$, $R^3$ and $R^4$ is hydrogen or $(C_1\text{-}C_{10})$ alkyl. In some embodiments, each of $R^1$, $R^2$, $R^3$ and $R^4$ is hydrogen or $(C_1\text{-}C_8)$ alkyl. In some embodiments, each of $R^1$, $R^2$, $R^3$ and $R^4$ is hydrogen or $(C_1\text{-}C_4)$ alkyl. In some embodiments, each of $R^1$, $R^2$, $R^3$ and $R^4$ is hydrogen or methyl. When $R^1$ is methyl and each of $R^2$, $R^3$, and $R^4$ is hydrogen, the cyclopropene is known herein as 1-methylcyclopropene (1-MCP).

In some embodiments, a cyclopropene is used that has boiling point at one atmosphere pressure of 50° C. or lower; or 25° C. or lower; or 15° C. or lower. Independently, in some embodiments, a cyclopropene is used that has boiling point at one atmosphere pressure of −100° C. or higher; −50° C. or higher; or −25° C. or higher; or 0° C. or higher.

The cyclopropenes applicable to this disclosure may be prepared by any method. Some suitable methods of preparation of cyclopropenes are the processes disclosed in U.S. Pat. Nos. 5,518,988 and 6,017,849. Any compound that is not a cyclopropene is known herein as a "non-cyclopropene."

The composition of present disclosure comprises at least one cyclopropene. The composition may be a gaseous composition, a liquid composition, or a solid composition.

Plants are subject to various biological processes such as, for example, growth, ripening, senescence, maturation, abscission, and degradation. Altering biological processes in plants or plant parts by contacting them with one or more chemical compositions is known as plant growth regulation. Chemical compositions that are effective at causing plant growth regulation are known herein as "plant growth regulators."

Some examples of classes of plant growth regulators that are not cyclopropenes are as follows:

(I) Ethylene, non-cyclopropene ethylene release agents, and non-cyclopropene compounds with high ethylene activity, including, for example, ethephon, abscisic acid, propylene, vinyl chloride, carbon monoxide, acetylene, or 1-butene.

(II) Non-cyclopropene compounds that inhibit ethylene synthesis or ethylene receptor site action or both, including, for example, aminoethoxyvinylglycine or aminooxyacetic acid.

(III) Non-cyclopropene compounds with cytokinin activity, including, for example, benzyl adenine, kinetin, zeatin, adenine, dihydrozeatin, tetrahydropyranylbenzyladenine, dimethylallyladenine, methylthiozeatin, ethoxyethyladenine, benzylamino benzimidazole, chlorophenylphenylurea, benzthiozolyoxyacetic acid, or fluorophenyl biuret compounds that elicit cytokinin response.

(IV) Non-cyclopropene auxins, including, for example, indoleacetic acid, indolepropionic acid, indolebutyric acid, naphthaleneacetic acid, beta-naphthoxyacetic acid, 4-chlorophenoxyacetic acid, 2,4-dichlorooxyacetic acid, trichlorophenoxyacetic acid, trichlorobenzoic acid, or 4 amino-3,5,6-trichloropicolinic acid.

(V) Gibberellins, including, for example, $GA_2$, $GA_3$, $GA_4$, $GA_5$, $GA_7$, and $GA_8$ having variously substituted giberellin backbone structures, helminthosporic acid, phaseolic acid, kaurenoic acid, or steviol.

(VI) Cofactors and inhibitors of IAA oxidase, including, for example, chlorogenic acid, coumaric acid, quercitin, or caffeic acid.

(VII) Non-cyclopropene secondary growth inhibitors, including, for example, methyl jasmonate.

(VIII) Non-cyclopropene natural growth hormones, including, for example, natural growth hormones derived from, for example, kelp, algae, or bacteria.

In some embodiments, the practice of the present disclosure involves the use of a composition comprising at least one cyclopropene and without using any plant growth regulator that is not cyclopropene. In some embodiments, the practice of the present disclosure involves the use of at least cyclopropene and the use of at least one plant growth regulator that is not a cyclopropene. Such embodiments may or may not use one or more members of the remaining classes of plant growth regulators that are not cyclopropenes. For example, embodiments are envisioned that do not use any member of class I (defined herein above), but such embodiments may or may not use one or member of any of classes II-VIII.

In some embodiments, the composition of present disclosure comprises the use of a composition comprising at least one cyclopropene and the use of a composition comprising at least one fungicidally active compound. Independently, in some embodiments, the composition of present disclosure does not include aminoethylvinylglycine. Independently, in some embodiments, the composition of present disclosure does not include any derivatives of vinylglycine.

Independently, in some embodiments, the composition does not include any compound that is a strobilurin. Strobilurins are known in the art and are defined, for example, by Harden et al. in WO 2005/044002.

In some embodiments, the composition of present disclosure has no abscission agent.

In the practice of the present disclosure, the composition may be contacted with a plant in a variety of ways. For example, the composition may be a solid, a liquid, a gas, or a mixture thereof.

In some embodiments, the composition of present disclosure is a gaseous composition. In such embodiments, crop plants may be surrounded by a normal ambient atmosphere (at approximately one atmosphere pressure) to which the composition of present disclosure has been added. In some embodiments, the concentration of cyclopropene is 0.1 nl/l (i.e., nanoliter per liter) or higher; or 1 nl/l or higher, or 10 nl/l or higher; or 100 nl/l or higher. Independently, in some embodiments, the concentration of cyclopropene is 3,000 nl/l or lower; or 1,000 nl/l or lower.

In some embodiments, the composition of present disclosure is a liquid composition. Such compositions may be liquid at a temperature of 25° C. In some embodiments, the composition is liquid at the temperature at which the composition is used to treat plants. Because plants are often treated outside of any buildings, plants may be treated at temperatures ranging from about 1° C. to about 45° C. Suitable liquid compositions need not be liquid over such entire range, but they are liquid at some temperature from about 1° C. to about 45° C.

The liquid composition of present disclosure may be a single pure substance, or it may contain more than one substance. If containing more than one substance, the liquid composition may be a solution or a dispersion or a combination thereof. If, in the liquid composition, one substance is dispersed in another substance in the form of a dispersion, the dispersion may be of any type, including, for example, a suspension, a latex, an emulsion, a miniemulsion, a microemulsion, or any combination thereof.

The amount of cyclopropene in the liquid composition may vary widely, depending on the type of composition and the intended method of use. In some embodiments, the amount of cyclopropene, based on the total weight of the composition, is 4% by weight or less; or 1% by weight or less; or 0.5% by weight or less; or 0.05% by weight or less. Independently, in some embodiments, the amount of cyclopropene, based on the total weight of the composition, is 0.000001% by weight or more; or 0.00001% by weight or more; or 0.0001% by weight or more; or 0.0010% by weight or more.

Among embodiments of the present disclosure that use a liquid composition comprising water, the amount of cyclopropene may be characterized as parts per million (i.e., parts by weight of cyclopropene per 1,000,000 parts by weight of water in the composition, "ppm") or as parts per billion (i.e., parts by weight of cyclopropene per 1,000,000,000 parts by weight of water in the composition, "ppb"). In some embodiments, the amount of cyclopropene is 1 ppb or more; or 10 ppb or more; or 100 ppb or more. Independently, in some embodiments, the amount of cyclopropene is 10,000 ppm or less; or 1,000 ppm or less.

In some embodiments, the composition may further include at least one molecular encapsulating agent. Independently, in some embodiments, the composition may not include any molecular encapsulating agent. When a molecular encapsulating agent is used, suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the disclosure, the encapsulating agent is alpha-cyclodextrin, beta-cyclodextrin, gamma-cyclodextrin, or a mixture thereof. In some embodiments, particularly when the cyclopropene is 1-methylcyclopropene, the encapsulating agent is alpha-cyclodextrin. The preferred encapsulating agent will vary depending upon the structure of the cyclopropene or cyclopropenes being used. Any cyclodextrin or mixture of cyclodextrins, cyclodextrin polymers, modified cyclodextrins, or mixtures thereof may also be utilized pursuant to the present disclosure. Some cyclodextrins are available, for example, from Wacker Biochem Inc., Adrian, MI or Cerestar USA, Hammond, IN, as well as other vendors.

In some of the embodiments in which a molecular encapsulating agent is present, at least one molecular encapsulating agent encapsulates one or more cyclopropenes. A cyclopropene or substituted cyclopropene molecule encapsulated in a molecule of a molecular encapsulating agent is known herein as a "cyclopropene molecular encapsulating agent complex." In some embodiments, the composition of present disclosure is a liquid composition in which some or all of the cyclopropene is encapsulated in one or more encapsulating agent. The cyclopropene molecular encapsulation agent complexes may be prepared by any means.

In one method of preparation, for example, such complexes are prepared by contacting the cyclopropene with a solution or slurry of the molecular encapsulation agent and then isolating the complex, using, for example, processes disclosed in U.S. Pat. No. 6,017,849. For example, in one method of making a complex in which 1-MCP is encapsulated in a molecular encapsulating agent, the 1-MCP gas is bubbled through a solution of alpha-cyclodextrin in water, from which the complex first precipitates and is then isolated by filtration. In some embodiments, complexes are made by the above method and, after isolation, are dried and stored in solid form, for example as a powder, for later addition to useful compositions.

In some embodiments, the composition comprises at least one cyclopropenes and at least one molecular encapsulating agent. In some of such embodiments, the amount of molecular encapsulating agent may usefully be characterized by the ratio of moles of molecular encapsulating agent to moles of cyclopropene. In some embodiments, the ratio of moles of molecular encapsulating agent to moles of cyclopropene is 0.1 or larger; or 0.2 or larger; or 0.5 or larger; or 0.9 or larger. Independently, in some of such embodiments, the ratio of moles of molecular encapsulating agent to moles of cyclopropene is 2 or lower; or 1.5 or lower.

In some embodiments, the composition may further include at least one ionic complexing reagent. An ionic complexing reagent interacts with a cyclopropene to form a complex that is stable in water. Some suitable ionic complexing reagents, for example, include lithium ion. In some embodiments, no ionic complexing reagent is used.

In some embodiments, the composition of present disclosure further includes one or more metal-complexing agents. In some embodiments, the compositions of the present disclosure do not include any metal-complexing agent. A metal-complexing agent is a compound that is capable of forming coordinate bonds with metal atoms. Some metal-complexing agents are chelating agents. As used herein, a "chelating agent" is a compound, each molecule of which is capable of forming two or more coordinate bonds with a single metal atom. Some metal-complexing agents form coordinate bonds with metal atoms because the metal-complexing agents contain electron-donor atoms that participate in coordinate bonds with metal atoms. Suitable chelating agents include, for example, organic and inorganic chelating agents. Among the suitable inorganic chelating agents are, for example, phosphates such as, for example, tetrasodium pyrophosphate, sodium tripolyphosphate, and hexametaphosphoric acid. Among the suitable organic chelating agents are those with macrocyclic structures and non-macrocyclic structures. Among the suitable macrocyclic organic chelating agents are, for example, porphine compounds, cyclic polyethers (also called crown ethers), and macrocyclic compounds with both nitrogen and oxygen atoms.

Some suitable organic chelating agents that have non-macrocyclic structures are, for example, aminocarboxylic acids, 1,3-diketones, hydroxycarboxylic acids, polyamines, aminoalcohols, aromatic heterocyclic bases, phenol, aminophenols, oximes, Shiff bases, sulfur compounds, and mixtures thereof. In some embodiments, the chelating agent includes one or more aminocarboxylic acids, one or more hydroxycarboxylic acids, one or more oximes, or a mixture thereof. Some suitable aminocarboxylic acids include, for example, ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis (hydroxyphenylglycine) (EHPG), and mixtures thereof. Some suitable hydroxycarboxylic acids include, for example, tartaric acid, citric acid, gluconic acid, 5-sulfoslicylic acid, and mixtures thereof. Some suitable oximes include, for example, dimethylglyoxime, salicylaldoxime, and mixtures thereof. In some embodiments, EDTA is used.

Some additional suitable chelating agents are polymeric. Some suitable polymeric chelating agents include, for example, polyethyleneimines, polymethacryloylacetones, poly(acrylic acid), and poly(methacrylic acid). Poly(acrylic acid) is used in some embodiments.

Some suitable metal-complexing agents that are not chelating agents are, for example, alkaline carbonates, such as, for example, sodium carbonate.

Metal-complexing agents may be present in neutral form or in the form of one or more salts. Mixtures of suitable metal-complexing agents are also suitable.

In some embodiments, the composition of present disclosure does not contain any water. In some embodiments, the composition of present disclosure contains water. In some of such embodiments, water may contain one or more metal ions, such as, for example, iron ions, copper ions, other metal ions, or mixtures thereof. In some embodiments, the water contains 0.1 ppm or more of one or more metal ions.

Among embodiments that use one or more metal-complexing agent, the amount of metal-complexing agent used may vary widely. In some embodiments in which at least one liquid composition is used, the amount of metal-complexing agent in that liquid composition will be adjusted to be sufficient to complex the amount of metal ion that is present or expected to be present in the liquid composition that contains the metal-complexing agent. For example, in some embodiments in which a liquid composition of the present disclosure is used that includes water that contains some metal ion, if a relatively efficient metal-complexing agent is used (i.e., a metal-complexing agent that will form a complex with all or nearly all the metal ions in the water), the ratio of moles of metal-complexing agent to moles of metal ion will be 0.1 or greater; or 0.2 or greater, or 0.5 or greater, or 0.8 or greater. Among such embodiments that use a relatively efficient metal-complexing agent, the ratio of moles of metal-complexing agent to moles of metal ion will be 2 or less; or 1.5 or less; or 1.1 or less. It is contemplated that, if a less-efficient metal-complexing agent is used, the ratio of moles of metal-complexing agent to moles of metal ion could be increased to compensate for the lower efficiency.

Independently, in some embodiments in which a liquid composition is used, the amount of metal-complexing agent is, based on the total weight of the liquid composition, 25% by weight or less; or 10% by weight or less; or 1% by weight or less. Independently, in some embodiments, the amount of metal-complexing agent is, based on the total weight of the liquid composition, 0.00001% or more; or 0.0001% or more; or 0.010% or more.

Independently, in some embodiments in which a liquid composition that includes water is used, the amount of metal-complexing agent may usefully be characterized by the molar concentration of metal-complexing agent in the water (i.e., moles of metal-complexing agent per liter of water). In some of such liquid compositions, the concentration of metal-complexing agent is 0.00001 mM (i.e., milliMolar) or greater; or 0.0001 mM or greater; or 0.001 mM or greater; or 0.01 mM or greater; or 0.1 mM or greater. Independently, in some embodiments in which a liquid composition of the present disclosure includes water, the concentration of metal-complexing agent is 100 mM or less; or 10 mM or less; or 1 mM or less.

In some embodiments, one or more adjuvants are also included in the composition of present disclosure. The use of adjuvants is considered optional in the practice of the present disclosure. Adjuvants may be used alone or in any combination. When more than one adjuvant is used, it is contemplated that any combination of one or more adjuvants may be used. Examples of suitable adjuvants may include, but are not limited to, surfactants, alcohols, oils, extenders, pigments, fillers, binders, plasticizers, lubricants, wetting agents, spreading agents, dispersing agents, stickers, adhesives, defoamers, thickeners, transport agents, or emulsifying agents.

In some embodiments, the composition of present disclosure contains at least one adjuvant selected from alcohols, oils, or mixtures thereof. Such a composition may or may not additionally contain one or more surfactant.

Among embodiments in which a liquid composition is used, any one or more of the following liquid composition may be used: liquid compositions that contain one or more surfactant but no oil and no alcohol; liquid compositions that contain one or more oil but no surfactant and no alcohol; or liquid compositions that contain one or more alcohol but no surfactant and no oil. In some embodiments, one or more liquid compositions are used that each contain one or more surfactant and one or more oil; or one or more liquid compositions are used that each contain one or more surfactant and one or more alcohol. In some embodiments, one or more liquid compositions are used that each contains one or more surfactant, one or more oil, and/or one or more alcohol.

In some embodiments, the liquid composition does not contain any organosilicate compound. In some embodiments, the liquid composition contains at least one organosilicate compound.

In some embodiments, one or more surfactants are used. Suitable surfactants include, for example, anionic surfactants, cationic surfactants, nonionic surfactants, amphoteric surfactants, or mixtures thereof. Mixtures of suitable surfactants may also be used. In some embodiments, one or more anionic surfactant is used.

One group of suitable anionic surfactants is the sulfosuccinates, including, for example, alkaline salts of mono- and dialkyl sulfosuccinates. In some embodiments, sodium salts of dialkyl sulfosuccinates are used, including, for example, those with alkyl groups with 4 carbons or more, or 6 carbons or more. In some embodiments, sodium salts of dialkyl sulfosuccinates are used, including, for example, those with alkyl groups with 18 carbons or fewer; or 14 carbons or fewer; or 10 carbons or fewer. Example of suitable sodium salt of a dialkyl sulfosuccinate is, for example, sodium di-hexyl sulfosuccinate. One other suitable sodium salt of a dialkyl sulfosuccinate is, for example, sodium di-octyl sulfosuccinate.

Another group of suitable anionic surfactants are the sulfates and sulfonates, including, for example, alkaline salts of alkyl sulfates. In some embodiments, sodium salts of alkyl sulfates are used, including, for example, those with alkyl groups with 4 carbons or more, or 6 carbons or more, or 8 carbons or more. In some embodiments, sodium salts of alkyl sulfates are used, including, for example, those with alkyl groups with 18 carbons or fewer; or 14 carbons or fewer; or 10 carbons or fewer. One suitable sodium salt of an alkyl sulfate is, for example, sodium dodecyl sulfate.

Some suitable surfactants are, for example, sodium di-octyl sulfosuccinate, sodium di-hexyl sulfosuccinate, sodium dodecyl sulfate, polyglycerol esters, alcohol ethoxylates, alkylphenol ethoxylates (such as, for example, TRITON™ X-100 from Dow), cetyl pyridinium bromide, ethoxylated alkyl amines, alcohol amines (such as, for example, ethanolamines), saponins, and silicone-based surfactants (such as, for example, SILWET™ L-77 surfactant from OSi Specialties).

Suitable surfactants have various properties. For example, some are excellent at enabling cyclopropene to remain in contact with certain plants or plant parts; some are readily soluble in the other ingredients of the formulation; some do not cause phytotoxicity in plants or plant parts. Very few surfactants excel in every property, but, when one or more surfactants are used, the practitioner will readily be able to choose a surfactant or mixture of surfactants with the balance of properties most appropriate for the desired use, taking into account, for example, the species desired to be treated and the other ingredients intended to be used in the composition.

Among embodiments in which one or more liquid compositions are used that include one or more surfactants, some liquid compositions contain surfactant in amounts, by weight based on the total weight of the liquid composition, of 0.025% or more; or 0.05% or more; or 0.1% or more. Independently, some liquid compositions use surfactant in amounts, by weight based on the total weight of the liquid composition, of 75% or less; or 50% or less; or 20% or less; or 5% or less; or 2% or less; 1% or less; or 0.5% or less; or 0.3% or less.

In some of the embodiments in which a liquid composition is used, no oil is included in the composition.

Independently, in some of the embodiments in which a liquid composition is used, one or more oils are used. As used herein, an "oil" is a compound that is liquid at a temperature of 25° C. and one atmosphere pressure, and that has a boiling point temperature of 30° C. or higher at one atmosphere pressure. As used herein, "oil" does not include water, does not include surfactants (as described herein above), and does not include alcohols (as described herein below). Some oils are hydrocarbon oils, while other oils are non-hydrocarbon oils. Hydrocarbon oils may be straight, branched, or cyclic alkane compounds with 6 or more carbon atoms. As used herein, "non-hydrocarbon" means and includes any compound that contains at least one atom that is neither hydrogen nor carbon.

In some embodiments in which a liquid composition is used, one or more hydrocarbon oils are included in the composition. In some embodiments, hydrocarbon oils are obtained from petroleum distillation and contain a mixture of alkane compounds, along with, in some cases, impurities. In some embodiments, hydrocarbon oils are used that contain 18 or fewer carbon atoms. Some suitable hydrocarbon oils include, for example, hexane, decane, dodecane, hexadecane, diesel oil, refined paraffinic oil such as ULTRAFINE™ spray oil from Sun Company, or mixtures thereof.

In some embodiments in which a liquid composition is used, one or more non-hydrocarbon oils are included in the composition. In some embodiments, non-hydrocarbon oils have boiling point temperature of 50° C. or higher; or 75° C. or higher; or 100° C. or higher. Independently, in some embodiments, non-hydrocarbon oils have molecular weight of 100 or higher; or 200 or higher; or 500 or higher.

Some suitable non-hydrocarbon oils are, for example, fatty non-hydrocarbon oils. The term "fatty" as used herein means and include any compound that contains one or more residues of fatty acids. Fatty acids are long-chain carboxylic acids, with chain length of at least four carbon atoms. Typical fatty acids have chain length of 4 to 18 carbon atoms, though some have longer chains. Linear, branched, or cyclic aliphatic groups may be attached to the long chain. Fatty acid residues may be saturated or unsaturated. Further, fatty acid residues may contain functional groups, including for example alkyl groups, epoxide groups, halogens, sulfonate groups, or hydroxyl groups, that are either naturally occurring or that have been added. Some suitable fatty non-hydrocarbon oils are, for example, fatty acids; esters of fatty acids; amides of fatty acids; dimers, trimers, oligomers, or polymers thereof; or mixtures thereof.

Some of the suitable fatty non-hydrocarbon oils, are, for example, esters of fatty acids. Such esters include, for example, glycerides of fatty acids. Glycerides are esters of fatty acids with glycerol, and they may be mono-, di-, or triglycerides. A variety of triglycerides are found in nature. Most of the naturally occurring triglycerides contain residues of fatty acids of several different lengths and/or compositions. Some suitable triglycerides are found in animal sources such as, for example, dairy products, animal fats, and fish. Further examples of suitable triglycerides are oils found in plants, such as, for example, coconut, palm, cottonseed, olive, tall, peanut, safflower, sunflower, corn, soybean, linseed, tung, castor, canola, citrus seed, cocoa, oat, palm, palm kernel, rice bran, cuphea, or rapeseed oil.

Among the suitable triglycerides, independent of where they are found or how they are made, are those, for example, that contain at least one fatty acid residue that has 14 or more carbon atoms. Some suitable triglycerides have fatty acid residues that contain 50% or more by weight, based on the weight of the residues, fatty acid residues with 14 or more carbon atoms, or 16 or more carbon atoms, or 18 or more carbon atoms. One example of a suitable triglyceride is soybean oil.

Suitable fatty non-hydrocarbon oils may be synthetic or natural or modifications of natural oils or a combination or mixture thereof. Among suitable modifications of natural oils are, for example, alkylation, hydrogenation, hydroxylation, alkyl hydroxylation, alcoholysis, hydrolysis, epoxidation, halogenation, sulfonation, oxidation, polymerization, and combinations thereof. In some embodiments, alkylated (including, for example, methylated and ethylated) oils are used. One suitable modified natural oil is methylated soybean oil.

Also among the suitable fatty non-hydrocarbon oils are self-emulsifying esters of fatty acids.

Another group of suitable non-hydrocarbon oils are silicone oils Silicone oils are oligomers or polymers that have a backbone that is partially or fully made up of —Si—O— links. Silicone oils include, for example, polydimethylsiloxane oils. Polydimethylsiloxane oils are oligomers or polymers that contain units of the form

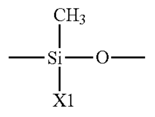

where at least one of the units has X1=$CH_3$. In other units, X1 may be any other group capable of attaching to Si, including, for example, hydrogen, hydroxyl, alkyl, alkoxy, hydroxyalkyl, hydroxyalkoxy, alkylpolyalkoxyl, substituted versions thereof, or combinations thereof. Substituents may include, for example, hydroxyl, alkoxyl, polyethoxyl, ether linkages, ester linkages, amide linkages, other substituents, or any combination thereof. In some suitable polydimethylsiloxane oils, all X1 groups are methyl. In some suitable polydimethylsiloxanes, at least one unit has an X1 group that is not methyl; if more than one non-methyl X1 unit is present, the non-methyl X1 units may be the same as each other, or two or more different non-methyl X1 units may be present. Polydimethylsiloxane oils may be end-capped with any of a wide variety of chemical groups, including, for example, hydrogen, methyl, other alkyl, or any combination thereof. Also contemplated are cyclic polydimethylsiloxane oils.

Mixtures of suitable oils may also be used, such as, for example, mixtures of plural hydrocarbon oils, mixtures of plural non-hydrocarbon oils, or mixtures of one or more hydrocarbon oil with one or more non-hydrocarbon oil.

Some embodiments use oil in amounts, by weight based on the total weight of the composition, of 0.25% or more; or 0.5% or more; or 1% or more. Independently, some embodiments use oil in amounts, by weight based on the total weight of the composition, of 90% or less; or 50% or less; or 10% or less; or 5% or less; or 4% or less; or 3% or less.

Among embodiments in which one or more liquid compositions are used, in some liquid compositions, one or more alcohols are used. Suitable alcohols include, for example, alkyl alcohols and other alcohols. As used herein, alkyl alcohols are alkyl compounds with one hydroxyl group; the alkyl group may be linear, branched, cyclic, or a combination thereof; the alcohol may be primary, secondary, or tertiary. In some embodiments, alkyl alcohols are used which have alkyl groups with 2 or more carbon atoms. In some embodiments, ethanol, isopropanol, or a mixture thereof is used. In some embodiments, one or more alkyl alcohols are used which have alkyl groups with 20 or fewer carbon atoms; or 10 or fewer carbon atoms; or 6 or fewer carbon atoms; or 3 or fewer carbon atoms.

Among liquid compositions that use alcohol, some liquid compositions use alcohol in amounts, by weight based on the total weight of the liquid composition, of 0.25% or higher; or 0.5% or higher, or 1% or higher. Among liquid compositions that use alcohol, some liquid compositions use alcohol in amounts, by weight based on the total weight of the liquid composition, of 90% or less; or 50% or less; or 10% or less; or 5% or less; or 4% or less; or 3% or less.

The ingredients of the disclosed composition may be admixed by any means, and in any order.

Disclosed herein are methods of treating crop plants that comprise contacting crop plants one or more times with a composition comprising at least one cyclopropene.

In the practice of the present disclosure, any method may be used that allows the disclosed composition to contact crop plants. Examples of such contact methods may include, for example, spraying, foaming, fogging, pouring, brushing, dipping, similar methods, or combinations thereof. In some embodiments, spraying or dipping or both is used. In some embodiments, spraying is used.

Among embodiments in which the disclosed composition is sprayed, any spray conditions may be used. For example, nozzle size and pressure may be chosen by the practitioner of the present disclosure to achieve desired results. Some useful nozzle types are, for example, flat fan, pre-orifice flat fan, hollow cone, full cone, air inclusion, low drift, or flooding. Independently, some useful spray pressures are, for example, 127 kPa (15 psi), 422 kPa (50 psi), 844 kPa (100 psi), 1689 kPa (200 psi), and 2534 kPa (300 psi). Spray pressures that are intermediate between any pair of these useful spray pressures are, in some embodiments, also useful. Independently, in some embodiments, the spray conditions are chosen to achieve certain droplet size; some useful droplet sizes are, for example, 50 micrometers, 100 micrometers, 200 micrometers, 300 micrometers, 400 micrometers, 600 micrometers, and 800 micrometers. Droplet sizes that are intermediate between any pair of these useful droplet sizes are, in some embodiments, also useful.

After crop plant is contacted with the disclosed composition, any ingredients of the disclosed composition that interact with the crop plant may begin that interaction right away. Alternatively, ingredients of the disclosed composition may, independently of each other, interact with the crop plant at a different time. For example, the liquid composition may form a release coating on all or part of the crop plant, and one or more ingredients may become available, over time, to interact with the crop plant.

In the practice of present disclosure, the composition may be contacted with the entire plant or may be contacted with one or more plant parts. Plant parts include any part of a plant, including, for example, flowers, buds, blooms, seeds, cuttings, roots, bulbs, fruits, vegetables, leaves, and combinations thereof.

In some embodiments, the composition of the present disclosure is a liquid, and the liquid is sprayed onto crop plants growing in a field. Such a spraying operation may be performed one time or more than one time on a particular group of crop plants during a single growing season. In some embodiments, the amount of cyclopropene used in one spraying operation is 0.1 gram per hectare (g/ha) or more; or 0.5 g/ha or more; or 1 g/ha or more; or 5 g/ha or more; or 25 g/ha or more; or 50 g/ha or more; or 100 g/ha or more. Independently, in some embodiments, the amount of cyclopropene used in one spraying operation is 6000 g/ha or less; or 3000 g/ha or less; or 1500 g/ha or less.

The disclosed composition may be applied to crop plants prior to the harvesting of the useful plant parts. If a composition is brought into contact with a portion of the plant, that portion may or may not include the useful plant part intended to be harvested. At least one treatment of crop plants with the disclosed composition may be performed before any useful plant parts are harvested.

The crop plants that are treated may be any crop plants that produce a useful product. Normally, a specific part of the plant forms the useful product. A plurality of useful plant parts, after removal from a plurality of plants, is known as a "crop." Some types of crop plants have a single type of useful plant part, while other types of crop plants have plural types of useful plant parts.

Among the crop plants that are suitable for use in the present disclosure are, for example, those with plant parts that are edible, those with plant parts that are non-edible but useful for some other purpose, and combinations thereof. Also contemplated as suitable crop plants are those from which useful materials can be extracted; such useful materials may be, for example, edible materials, raw materials for manufacturing, medicinally useful materials, and materials useful for other purposes.

Further contemplated as suitable crop plants are those that yield plant parts that are useful for their beauty and/or ornamental properties. Such ornamental plant parts include, for example, flowers and other ornamental plant parts such as, for example, ornamental leaves. Some of such plants produce useful bulbs. In some embodiments, an entire ornamental plant is considered to be the useful plant part.

Also suitable are crop plants that produce edible plant parts. Crop plants that produce all types of edible plant parts are contemplated as suitable for use in the present disclosure.

Suitable crop plants for present disclosure may be crop plants that produce fruits, vegetables, spices, herbs, or plants or plant parts grown for ornamental use. In some embodiments, crop plants produce fruits or vegetables. In some embodiments, crop plants produce vegetables.

Many of the plants that are suitable for use in the practice of the present disclosure can be usefully divided into categories or groups. One useful method for defining such groups is the "Definition and Classification of Commodities," published on or before Mar. 23, 2006, by the Food and Agriculture Organization ("FAO") of the United Nations as a "Draft."

In some embodiments of the present disclosure, the crop plants may produce one or more crops that fall within any one of the following crop groups.

Also contemplated are embodiments in which crop plants that produce two or more crops are used. In such embodiments, a single crop plant type that produces two or more crops may be used, or a mixture of two or more plants that produce different crops from each other may be used, or any combination thereof. Independently, if two or more crops are used, they may be from the same crop group or from different crop groups.

Crop Group 1 is cereals, including, for example, wheat, rice, barley, corn, popcorn, rye, oats, millet, sorghum, buckwheat, quiona, fonio, triticale, canary seed, canagua, quihuicha, adlay, wild rice, and other cereals. In some embodiments of the present disclosure, suitable plants are those that produce wheat or rice or corn or sorghum. In some embodiments, corn plants are suitable. In some embodiments, wheat plants are suitable.

Crop Group 2 roots and tubers, including, for example, potatoes, sweet potatoes, cassava, yautia (cocomay), taro (cocoyam), yams, and other roots and tubers. Also considered herein as a suitable root crop is Chinese water chestnut (*Eleocharis dulcis*).

Crop Group 3 is sugar crops, including, for example, sugar cane, sugar beet, sugar maple, sweet sorghum, sugar palm, and other sugar crops.

Crop Group 4 is pulses, including, for example, beans (including, for example, kidney, haricot, lima, butter, adzuki, mungo, golden, green gram, black gram, urd, scarlet runner, rice, moth, tepary, lablab, hyacinth, jack, winged, guar, velvet, yam, and other beans), horse-bean, broad bean, field bean, garden pea, chickpea, bengal gram, garbanzo, cowpea, blackeyed pea, pigeon pea, cajan pea, congo bean, lentil, bambara ground nut, earth pea, vetches, lupins, and other pulses.

Crop Group 5 is nuts, including, for example, brazil nuts, cashew nuts, chestnuts, almonds, walnuts, pistachios, kola nuts, hazelnuts, areca nuts, pecan nut, butter nut, pili nut, Java almond, paradise nut, macadamia nut, pignolia nut, and other nuts.

Crop Group 6 is oil-bearing crops, including, for example, soybeans, groundnuts (including peanuts), coconuts, oil palm fruit, olives, karite nuts, castor beans, sunflower seeds, rapeseed, canola, tung nuts, safflower seed, sesame seed, mustard seed, poppy seed, melonseed, tallowtree seeds, kapok fruit, seed cotton, linseed, hempseed, and other oilseeds. In some embodiments, soybean plants are suitable.

Crop Group 7 is vegetables, including, for example, cabbages, artichokes, asparagus, lettuce, spinach, cassava leaves, tomatoes, cauliflower, pumpkins, cucumbers and gherkins, eggplants, chilies and peppers, green onions, dry onions, garlic, leek, other alliaceous vegetables, green beans, green peas, green broad beans, string beans, carrots, okra, green corn, mushrooms, watermelons, cantaloupe melons, bamboo shoots, beets, chards, capers, cardoons, celery, chervil, cress, fennel, horseradish, marjoram, oyster plant, parsley, parsnips, radish, rhubarb, rutabaga, savory, scorzonera, sorrel, watercress, and other vegetables.

Crop Group 8, is fruits, including, for example, bananas and plantains; citrus fruits; pome fruits; stone fruits; berries; grapes; tropical fruits; miscellaneous fruits; and other fruits. Citrus fruits include, for example, orange, tangerine, mandarin, clementine, satsumas, lemon, lime, grapefruit, pomellow, bergamot, citron, chinotto, kumquat, and other citrus fruits. Pome fruits include, for example, apple, pear, quince, and other pome fruits. Stone fruits include, for example, apricot, cherry, peach, nectarine, plum, and other stone fruits. Berries include, for example, strawberry, raspberry, gooseberry, currant, blueberry, cranberry, blackberry, loganberry, mulberry, myrtle berry, huckleberry, dangleberry, and other berries. Tropical fruits include, for example, fig, persimmon, kiwi, mango, avocado, pineapple, date, cashew apple, papaya, breadfruit, carambola, chrimoya, durian, feijoa, guava, mombin, jackfruit, longan, mammee, mangosteen, naranjillo, passion fruit, rambutan, sapote, sapodilla, star apple, and other tropical fruits. Miscellaneous fruits include, for example, azarole, babaco, elderberry, jujube, litchi, loquat, medlar, pawpaw, pomegranate, prickly pear, rose hips, rowanberry, service-apple, tamarind, and tree-strawberry.

Crop Group 9 is fibers, including, for example, cotton, flax, hemp, kapok, jute, ramie, sisal, and other fibers from plants. In some embodiments, cotton plants are suitable.

Crop Group 10 is spices, including, for example, pepper, pimento, vanilla, cinnamon, nutmeg, mace, cardamon, cloves, anise, badian, fennel, ginger, bay leaves, dill seed, fenugreek seed, saffron, thyme, turmeric, and other spices.

Crop Group 11 is Fodder crops. Fodder crops are crops that are cultivated primarily for animal feed. Natural grasslands and pastures are included in crop group 11, whether they are cultivated or not. Fodder crops also include, for example, corn for forage, sorghum for forage, rye grass for forage, clover for forage, alfalfa for forage, other grasses for forage, green oilseeds for silage, legumes for silage, other crops for silage, cabbage for fodder, pumpkins for fodder, turnips for fodder, beets for fodder, carrots for fodder, swedes for fodder, other vegetables or roots for fodder, and other fodder crops.

Crop Group 12 is stimulant crops, including, for example, coffee, cocoa bean, tea, mate, other plants used for making infusions like tea, and other stimulant corps.

Crop Group 13 is tobacco and rubber and other crops, including, for example, chicory root, carob, hops, oil of citronella, peppermint, spearmint, other plant oils used in perfumery, food, and other industries, pyrethrum, tobacco, natural rubber, natural gums (including, for example, balata, cerea, chicle, guayule, gutta-percha, and jelutong), other resins (including, for example, copaiba, gum tragacanth, incense, myrrh, opopanax, mecca balsom, tolu balsam, and peru balsam), and vegetable waxes (including, for example, candelilla, carnauba, urucury, and palm wax).

In some embodiments, the present disclosure involves treatment of any non-citrus plant (i.e., any plant that is not in the genus Citrus).

In some of the embodiments in which apple trees are used, the composition of present disclosure contains no aminoethoxyvinylglycine, or, in some embodiments, no plant growth regulator of type II defined herein above, or, in some embodiments, no plant growth regulator that is not a cyclopropene. In other embodiments, no apple trees are used in the practice of the present disclosure. In some embodiments, no pome fruit trees are used in the practice of the present disclosure.

In some embodiments, the treated crop plants are not members of the genus *Nicotiana.*

In some embodiments, crop plants that are contacted with the composition of present disclosure include one or more of corn, soybean, cotton, apple, pear, rice, wheat, tomato, grape, sorghum, plum, kiwi, walnut, almond, pecan, sunflower, oilseed rape, canola, barley, rye or triticale. In some embodiments, crop plants that are contacted with the composition of present disclosure include one or more of corn, soybean, cotton, apple, pear, rice, wheat, tomato, grape or sorghum. In some embodiments, crop plants that are contacted with the composition of present disclosure include one or more of corn, soybean, cotton or wheat.

In some embodiments, the crop plants that are treated are any crop plants that produce a horticultural crop. Horticultural crops are agricultural products that are not agronomic crops and are not forestry products. Agronomic crops are herbaceous field crops, including grains, forages, oilseeds, and fiber crops. Forestry products are forest trees and forest products. Horticultural crop plants are usually relatively intensively managed crop plants that are cultivated for food or for aesthetic purposes. Some typical horticultural crops are fruits, vegetables, spices, herbs, and plants grown for ornamental use.

Some embodiments involve treatment of solanaceous plants or cucurbit plants. Solanaceous plants include, for example, *Lycopersicon esculentum* plants (including, for example, tomato plants); capsicum plants (including, for example, bell pepper, paprika, and chile pepper plants); and *Solanum melongena* plants (including, for example, eggplant, aubergine, or brinjal plants). Cucurbit plants include, for example, *Citrullus lanatus* (watermelon) plants, *Cucumis sativus* (cucumber) plants, *Cucumis melo* (all types of melon) plants, *Cucumis anguria* (bur gherkin) plants, *Cucurbita* (five species of squash & pumpkin) plants, *Cucurbita pepo* (summer squashes, pumpkin, scallops, straightnecks, zucchini, yellow-flowered gourd) plants, *Cucurbita maxima* (hubbard) plants, *Cucurbita mixta* (winter squash) plants, and *Cucurbita moschata* (butternut squash, banana squashes, and acorn squash) plants.

In some embodiments, the amount of cyclopropene is chosen to be appropriate for the particular crop that is being treated. For example, in some of the embodiments in which the crop plants are corn or soybean, the amount of cyclopropene is 500 g/ha or less, or 250 g/ha or less, or 100 g/ha or less, or 50 g/ha or less. For another example, in some of the embodiments in which the crop plants are cotton, the amount of cyclopropene is 50 g/ha or more, or 100 g/ha or more, or 200 g/ha or more.

In some embodiments, a group of crop plants is treated simultaneously or sequentially. One characteristic of such a group of plants is the crop yield, which is defined as the amount (herein called "crop amount") of useful plant parts collected from a defined group of plants. In one useful definition of the crop yield, the defined group of plants is the group that occupies a certain area of ground (this definition is often used when plants are growing in a contiguous group in a field). In another useful definition of the crop yield, the defined group of plants is a specific number of individually identified plants (this definition may be used for any group of plants, including, for example, plants in fields, in pots, in greenhouses, or any combination thereof).

The crop amount may defined in a variety of ways. In the practice of the present disclosure, the crop amount may be measured, for example, by any of the following methods: weight, volume, number of harvested plant parts, or biomass. Also contemplated are methods in which the crop amount is measured as the amount in the crop of a specific constituent (such as, for example, sugar, starch, or protein). Further contemplated are methods in which the crop amount is measured as the amount of a certain characteristic (such as, for example, redness, which is sometimes used to measure the amount of a crop of tomatoes). Additionally contemplated are methods in which the crop amount is measured as the amount of a specific portion of the harvested plant part (such as, for example, the number of kernels or the weight of kernels, which are sometimes used to measure the amount of a crop of corn; or the weight of lint, which is sometimes used to measure the amount of a cotton crop).

In some embodiments, the crop yield is defined as the crop amount per unit of area of land. That is, the land area from which the crop was harvested is measured, and the crop amount is divided by the land area to calculate the crop yield. For example, a crop amount measured as the weight of harvested plant parts would lead to a crop yield that is reported as a weight per area (for example, kilograms per hectare).

In some embodiments, the harvested plant parts that contribute to the crop amount are those plant parts that meet the minimum quality criteria that are appropriate for that type of plant part. That is, when plant parts are harvested from certain plants, the crop amount is, for example, the weight of the plant parts of acceptable quality that are harvested from those plants. Acceptable quality may be determined by any of the common criteria used by persons who harvest or handle the plant part of interest. Such criteria of acceptable quality of a plant part may be, for example, one or more of size, weight, firmness, resistance to bruising, flavor, sugar/starch balance, color, beauty, other quality criteria, or any combination thereof. Also contemplated as a criterion of quality, either alone or in combination with any of the foregoing criteria, is the time over which the plant part maintains its quality (as judged by any of the forgoing criteria).

A few illustrative (but not limiting) examples of crop amount are, for example, total weight of crop harvested; total number of plant parts harvested; weight (or number) of harvested plant parts that each meet or exceed some minimum weight for that type of plant part; or weight (or number) of harvested plant parts that each meet or exceed some minimum quality criterion (e.g., color or flavor or texture or other criterion or combination of criteria) for that type of plant part; weight (or number) of harvested plant parts that are edible; or weight (or number) of harvested plant parts that are able to be sold. In each case, as defined herein above, the crop yield is the crop amount per unit area of land on which the crop was grown.

The methods of present disclosure may increase the crop yield of that group of plants, compared to the crop yield that would have been obtained from that group of plants if it had not been treated with the methods of present disclosure. The increase in crop yield may be obtained in any of a wide variety of ways. For example, one way an increase in crop yield may be obtained is that each plant may produce a greater number of useful plant parts. As another example, one way an increase in crop yield may be obtained is that each useful plant part may have higher weight. As a third example, crop yield may increase when a larger number of potentially useful plant parts meets the minimum criteria for acceptable quality. Other ways of increasing the crop yield may also result from the practice of the present disclosure. Also contemplated are increases in crop yield that happen by any combination of ways.

Another contemplated benefit of practicing some embodiments of the present disclosure is that the general quality of the crop may be improved. That is, a crop produced by the methods of present disclosure may have a general or average level of quality higher than comparable crops produced without the methods of present disclosure, as judged by the quality criteria appropriate for that crop. In some cases, such higher-quality crops may command higher prices when sold.

The improvement in crop yield caused by the methods of present disclosure may arise by any mechanism. That is, the methods of present disclosure, in some embodiments, may cause an improvement in some process of the plant's development, maturation, growth, or reproduction, and such improvement in such process may, in turn, cause improvement in crop yield. For example, the methods of present disclosure may cause an improvement in any one or any combination of the following processes: synchronization of pollination (i.e., better agreement between the time period when a plant sheds pollen and the time period when that plant is able to receive the pollen and become fertilized), photosynthesis, nitrogen accumulation, leaf senescence, or late-season production of green leaves. In some of the embodiments where photosynthesis is improved, the improvement in photosynthesis can be observed as increased assimilation of carbon dioxide. Independently, the improvement in crop yield may, in some embodiments, occur because of improvement in disease resistance or drought resistance or frost resistance or heat resistance or a combination thereof.

In some crops (such as, for example, corn), it is contemplated that drought resistance and the resultant improvement in crop yield arise because the methods of present disclosure causes stomatal closure, which gives the plant its resistance to drought. Independently, some crops (such as, for example, wheat) experience improved frost tolerance when used in the methods of present disclosure. Independently, some crops (such as, for example, wheat and grapes) experience improved resistance to disease when used in the methods of present disclosure.

Independently, in some embodiments, improvement in crop yield may occur because of a delay in the dropping of one or more of leaves, flowers, or fruiting structures (such as, for example, pods, bolls, or the fruit itself).

Independently, in some embodiments, improvement in crop yield may occur because of enhanced root nodulation, which sometimes occurs in certain crops such as, for example, soybeans.

Whether or not the methods of present disclosure results in improvement in one or more of the above-mentioned processes, in some embodiments the methods of present disclosure leads to improvement in one or more of the following: biomass volume, biomass quality, increased fruit, increased fruit size (when desired), decreased fruit size (when desired), harvest timing (advanced or delayed, as desired), reduced fruit drop, decreased cell turgor, decreased russetting, lowered stress response, lowered wounding response, reduced storage disorders in harvested plant parts, increased shelf life of harvested plant parts, apical dominance, abscission prevention, senescence prevention, yellowing prevention, improved vigor during growth, improved vigor during transit, improved vigor during transplant, or combinations thereof.

The growth and development process of many crop plants can be described by certain developmental stages. For example, many crop plants develop through vegetative stages followed by reproductive stages.

It has been found now that surprisingly and unexpectedly, for some specific crop plants, there is a particular optimum stage or stages of crop plants at which the maximum improvement in crop yield may be achieved if crop plants are treated with the disclosed composition while they are in such particular optimum stage(s). This optimum stage or stages may be different for each type of crop plant and, in some cases, depends on the specific growing conditions.

Thus, in one aspect of the present disclosure, a method of treating crop plants comprises contacting crop plants one or time with a composition comprising at least one cyclopropene, while the crop plants are at a particular optimum stage of development to achieve a maximum crop yield. It is contemplated that such contacting may be performed when the ratio of the number of plants that have reached the desired stage of development to the total number of plants in the group is at least 0.1, or at least 0.5, or at least 0.75, or at least 0.9 (i.e., when the portion of plants that have reached the desired stage of development is at least 10%, or 50%, or 75%, or 90%).

In some embodiments, crop plants are contacted with the composition of present disclosure one or more times, while the crop plants are at one or more vegetative stages.

In some embodiments, crop plants are contacted with the composition of present disclosure one or more times, while the crop plants are one or more reproductive stages.

Also contemplated are embodiments in which crop plants are contacted with the composition of present disclosure one or more times while the crop plants are at one or more vegetative stages, and also contacted with the composition of present disclosure one or more times while the crop plants are at one or more reproductive stages.

Some crop plants develop through ripening stages after their reproductive stages. In some embodiments, such crop plants are contacted one or more tune with the composition of present disclosure while the crop plants are at one or more ripening stage, either in addition to or instead of while the crop plants are other development stages.

Some crop plants develop through vegetative and reproductive processes simultaneously. Such crop plants may be contacted one or more times with the composition of present disclosure after their germination but before harvest.

One particular embodiment of present disclosure is directed to methods of treating soybean plants.

Soybean plants develop through vegetative stages followed by reproductive stages. Some of the vegetative stages are VE (emergence), VC (cotyledon), V1 (fully developed leaves at unifoliate node), and VN ("N" is the number of nodes on the main stem that have fully developed leaves). Some of the reproductive stages are R1 (beginning bloom), R2 (full bloom), R3 (beginning pod), R4 (full pod), R5 (beginning seed), R5.5 (intermediate between R5 and R6), R6 (full seed), R7 (beginning maturity), and R8 (full maturity).

In some embodiments, soybean plants are contacted with the composition of present disclosure one or more times during one or more of any vegetative stage, one or more of any reproductive stage, or any combination thereof. In some embodiments, soybean plants are contacted with the composition of present disclosure during one or more of V3, V4, V5, or V6 and, optionally, also one or more times during one or more reproductive stage. In some embodiments, soybean plants are contacted with the composition of present disclosure one or more times during R1, R2, R3, R5, or R5.5. Independently, in some embodiments, soybean plants are contacted with the composition of present disclosure one or more times during or after stage V3 and, optionally, at one or more later stages. Independently, in some embodiments, soybean plants are contacted with the composition of present disclosure one or more times during or after stage R1 and, optionally, at one or more later stages. Independently, some embodiments involve contacting soybean plants with a liquid composition comprising at least one cyclopropene, after at least 10% of said soybean plants have at least one node on the main stem with at least one fully developed leaf. Some embodiments involve contacting soybean plants one or more times with a liquid composition comprising at least one cyclopropene, after at least 10% of soybean plants have begun to bloom.

In one particular embodiment, a method of treating soybean plants comprises contacting soybean plants one or more time with a composition comprising at least one cyclopropene while the soybean plants are at a reproductive stage of R2 (full bloom), R3 (beginning pod), R5.5 (between beginning seed and full seed), or a combination of any of these reproductive stages.

As shown in Example 1, infra, soybean plants are treated with a composition comprising 1-MCP at different dosages and while the soybean plants are at different reproductive stages. TABLE 1 below summarizes the results of Example 1.

TABLE 1 shows increases in % crop yield, compared to the soybean plants that are not treated with a composition comprising 1-MCP, for the soybean plants treated with the composition while the soybean plants at different development stages: reproductive stage of R2 (full bloom), R3 (beginning pod), R5.5 (between beginning seed and full seed), or a combination of any of these reproductive stages.

TABLE 1

| Soybean Plants | Development Stage(s) at which the Composition is applied | % Increase in Crop Yield |
|---|---|---|
| Untreated | n/a | 0.00% |
| Treated with Adjuvant Oil | R2, R3, and R5.5 | 1.51% |
| Treated with | R2 | 2.34% |
| Disclosed Composition | R3 | 5.22% |
| at 1-MCP Dosage of 1 g/ha | R5.5 | 1.46% |
| | R2 and R3 | 4.97% |
| | R2 and R5.5 | 2.68% |
| | R3 and R5.5 | 4.34% |
| | R2, R3, and R5.5 | 9.66% |
| Treated with | R2 | 1.79% |
| Disclosed Composition | R3 | 4.17% |
| at 1-MCP Dosage of 10 g/ha | R5.5 | 3.16% |
| | R2 and R3 | 7.36% |
| | R2 and R5.5 | 5.84% |
| | R3 and R5.5 | 5.11% |
| | R2, R3, and R5.5 | 14.20% |
| Treated with | R2 | 2.63% |
| Disclosed Composition | R3 | 3.88% |
| at 1-MCP Dosage of 30 g/ha | R5.5 | 5.84% |
| | R2 and R3 | 14.18% |
| | R2 and R5.5 | 6.58% |
| | R3 and R5.5 | 9.41% |
| | R2, R3, and R5.5 | 20.51% |

As shown in TABLE 1, an increase in crop yield is achieved when the soybean plants are contacted with a composition comprising 1-MCP while they are at a reproductive stage of R2 (full bloom), R3 (beginning pod), R5.5 (between beginning seed and full seed), or a combination of any of these reproductive stages.

Surprisingly and unexpectedly, the magnitude of crop yield enhancement depends on the development stage at which the soybean plants are contacted with a composition comprising 1-MCP. Even though an increase in the soybean crop yield is achieved when the soybean plants are treated with a composition comprising 1-MCP, the application of the composition while soybean plants are at the reproductive stage of R3 (beginning pod), or a combination of R3 with R2 (full bloom) and/or R5.5 (between beginning seed and full seed), appears to be more effective for enhancing the soybean crop yield.

Further, as shown in Example 1, treatment of soybean plants with a composition comprising 1-MCP while the soybean plants are at the reproductive stage of R2 (full bloom), R3 (beginning pod) and/or R5.5 (between beginning seed and full seed) also improve the protein content of the harvested soybean crops.

One particular embodiment of present disclosure is directed to methods of treating corn plants.

Corn plants develop through vegetative stages followed by reproductive stages. The vegetative growth stages of corn plants include VE (emergence), V1 (emergence of first leaf), VN (emergence of Nth leaf), VNMAX (emergence of last leaf), and VT (tasselling). One of these vegetative stages is V5, which begins when the fifth leaf emerges. Another of these vegetative stages is V12, which begins when the twelfth leaf emerges. The reproductive growth stages of corn plants include R1 (silking), R2 (blister), R3 (milk), R4 (dough), R5 (dent), R6 (maturity).

In some embodiments, corn plants are contacted with the composition of present disclosure during or after any of V5 (emergence of fifth leaf), V12 (emergence of 12th leaf), VT, R3, or during or after any combination of two or more of V6, V12, VT, and R3. Independently, in some embodiments, corn plants are contacted with the composition of present disclosure during V12, during VT, and during R3. Independently, some embodiments involve spraying corn plants one or more times with a liquid composition comprising at least one cyclopropene, after at least 10% of said corn plants have reached the developmental stage at which the fifth leaf is fully expanded, or after at least 10% of said corn plants have reached the developmental stage at which the twelfth leaf is fully expanded.

In one particular embodiment, a method of treating corn plants comprises contacting corn plants one or more time with a composition comprising at least one cyclopropene while the corn plants are at a development stage of V12 (the twelfth leaf emerges), VT (tasselling), R3 (milk), or a combination of any of these reproductive stages.

As shown in Example 2, infra, corn plants are treated with a composition comprising 1-MCP at different dosages of 1-MCP and while the corn plants are at different development stages. TABLE 2 summarizes the results of Example 2.

TABLE 2 shows the increases in both crop yield and kernel weight for the corn plants treated with a composition comprising 1-MCP, compared to the untreated corn plants, while the corn plants are at different development stages: reproductive stage of V12 (the twelfth leaf emerges), VT (tasselling), R3 (milk), or a combination of any of these reproductive stages.

TABLE 2

| Corn Plants | Development Stage(s) at which the Composition is applied | % Increase in Crop Yield | % Increase in Kernel Weight |
|---|---|---|---|
| Untreated | n/a | 0.00% | 0.00% |
| Treated with | V12 | 9.76% | 7.26% |
| Disclosed Composition | VT | 13.41% | 7.66% |
| at 1-MCP Dosage of 10 g/ha | R3 | 10.37% | 6.85% |
| | V12, VT | 10.98% | 6.05% |
| | VT, R3 | 4.88% | 9.27% |
| | V12, VT, R3 | 3.66% | 4.44% |
| Treated with | V12 | 12.20% | 8.87% |
| Disclosed Composition | VT | 14.02% | 11.69% |
| at 1-MCP Dosage of 10 g/ha | R3 | 10.98% | 6.85% |

As shown in TABLE 2, increases in both crop yield and kernel weight are achieved when the corn plants are contacted with a composition comprising 1-MCP while they are at a development stage of V12 (the twelfth leaf emerges), VT (tasselling), R3 (milk), or a combination of any of these reproductive stages. However, the magnitudes of enhanced crop yield and increased kernel weight depend on the development stage at which the corn plants are contacted with a composition comprising 1-MCP. The treatment of corn plants with a composition comprising 1-MCP while the corn plants are at VT (tasselling) stage appears to be more effective for enhancing the crop yield and kernel weight, compared to V12 (the twelfth leaf emerges) or VT (tasselling), R3 (milk) stage.

One particular embodiment of present disclosure is directed to methods of treating cotton plants.

Cotton plants are believed to simultaneously produce vegetative and fruiting structures. However, cotton plants develop through well-known stages. One such stage is the emergence of seedlings. The subsequent stages are marked by the appearance of pinhead squares and then blooming.

In some embodiments, cotton plants are contacted one or more times with the composition of present disclosure after seedling emergence. In some embodiments, cotton plants are contacted one or more times with the composition of present disclosure soon (i.e., three days or less) after the appearance of pinhead squares. In some embodiments, cotton plants are contacted with the composition of present disclosure soon after the appearance of pinhead squares and are then subsequently contacted with the composition of present disclosure again at one or more later time (i.e., 7 days or more after the previous treatment).

Independently, some embodiments involve spraying cotton plants one or more times with a liquid composition comprising at least one cyclopropene, after at least 10% of said cotton plants have developed pinhead squares.

In one particular embodiment, a method of treating cotton plants comprises contacting cotton plants one or more time with a composition comprising at least one cyclopropene at no more than 3 days after the appearance of pinhead squares or early bloom on the cotton plants, then contacting the corn plants with the composition again at 14 days after the first contact, and optionally contacting the corn plants with the composition one more time at 28 days after the first contact.

In one further particular embodiment, a method of treating cotton plants comprises contacting cotton plants with a composition comprising at least one cyclopropene at no more than 3 days after the appearance of early bloom on the cotton plants, then contacting the corn plants with the composition again at 14 days after the first contact, and further contacting the cotton plants with the composition at 28 days after the first contact.

Cotton plants are treated with a composition comprising 1-MCP while the cotton plants are at different development stages as shown in TABLE 3 below and Example 3, infra.

TABLE 3

| Treatment Type | First Treatment | Second Treatment | Third Treatment |
|---|---|---|---|
| PHS 2 | soon after appearance of pinhead squares | 14 days after first treatment | none |
| PHS 3 | soon after appearance of pinhead squares | 14 days after first treatment | 28 days after first treatment |
| EB 2 | soon after appearance of early bloom | 14 days after first treatment | none |
| EB 3 | soon after appearance of early bloom | 14 days after first treatment | 28 days after first treatment |

TABLE 4 shows the percentage increase in lint yield for the cotton plants treated with the a composition comprising 1-MCP according to the treatment types as shown in TABLE 3, and at different dosages of 1-MCP (250 g/ha, 500 g/ha, and 1250 g/ha), in comparison the untreated cotton plants.

The crop yield was assessed as the weight of lint per hectare. Treatment types, treatment amounts (grams of 1-MCP per hectare), and results were as follows. Many of the treatments lead to improvements in the yield of lint.

TABLE 4

| Dosage of 1-MCP (g/ha) | Treatment Type | % Increase in Lint Yield |
|---|---|---|
| 0 | Untreated | 0.00% |
| 250 | PHS 2 | 1.14% |
| | PHS 3 | 1.67% |
| | EB 2 | 7.59% |
| | EB 3 | 9.74% |
| 500 | PHS 2 | 12.98% |
| | PHS 3 | 14.91% |
| | EB 2 | 2.72% |
| | EB 3 | 14.61% |

TABLE 4-continued

| Dosage of 1-MCP (g/ha) | Treatment Type | % Increase in Lint Yield |
|---|---|---|
| 1250 | PHS 2 | 11.36% |
| | PHS 3 | 5.88% |
| | EB 2 | 3.07% |
| | EB 3 | 14.34% |

As shown in TABLE 4, an increase in lint yield from cotton plants is achieved when the cotton plants are contacted with a composition comprising 1-MCP. However, the lint yield depends on the development stage at which the cotton plants are contacted with the composition comprising 1-MCP. The most improved lint yield is obtained from the cotton plants that are treated with the composition comprising 1-MCP at no more than 3 days after the appearance of early bloom on the cotton plants, then again at 14 days after the first treatment, and again at 28 days after the first treatment.

One embodiment of present disclosure is directed to methods of treating wheat plants.

Wheat plants grow through developmental stages that are commonly described with the well-known Feekes scale. In the practice of the present disclosure, wheat plants may be contacted one or more times with the composition of present disclosure during one or more stages on the Feekes scale, or during any combination thereof. Some of the stages on the Feekes scale are, for example, F8.0 (flag leaf visible), F9.0 (ligule of flag leaf visible), F10.0 (boot stage), and F10.5 (heading complete). In some embodiments, wheat plants are contacted with the composition of present disclosure during or after any one or more of F8.0, F9.0, F10.0, or F10.5. In some embodiments, wheat plants are contacted with the composition of present disclosure during two or more of F8.0, F9.0, F10.0, and F10.5. In some embodiments, wheat plants are contacted with the composition of present disclosure during each of F8.0, F9.0, F10.0, and F10.5. Independently, in some embodiments, wheat plants are contacted with the composition of present disclosure at least once after at least 10% of the wheat plants have reached F9.0 growth stage. Independently, some embodiments involve spraying wheat plants one or more times with a liquid composition comprising at least one cyclopropene, after at least 10% of the wheat plants have reached the developmental stage at which the flag leaf is visible.

In some embodiments, wheat plants are treated that are selected from one or more varieties that do not include either or both of the varieties Halberd and Karl92. In some embodiments, the plants that are treated do not include wheat.

As shown in Example 4, infra, an increased crop yield, as well as an improved resistance to frost damage and disease damage is achieved by contacting wheat plants with the composition comprising 1-MCP while the wheat plants are at the developmental stage of F10.5 (heading complete).

One particular embodiment of present disclosure is directed to methods of treating tomato plants. Suitable tomato plants may include, but not limited to, processing tomato plants or fresh market tomato plants.

Tomato plants are treated at least one time with at least one treatment taking place at any time during any reproductive stage. In some embodiments, tomato plants are treated at one or more of the following times: at the initiation of the first bloom period; seven days after the initiation of the first bloom period, 28 days before anticipated harvest, 21 days before anticipated harvest, 14 days before anticipated harvest, and any combination thereof. The suitable treatment rates include, for example, 5 g/ha or more; or 10 g/ha or more; or 20 g/ha or more. Independently, among embodiments involving treatment of tomato plants, suitable treatment rates include, for example, 100 g/ha or less; or 60 g/ha or less; or 30 g/ha or less.

In one particular embodiments, a method of treating tomato plants comprises contacting tomato plants with a composition comprising at least one cyclopropene at one or more of the following times: during the period from initiation of the first bloom period to seven days after the initiation of the first bloom period; and one or more times during the period from 28 days before anticipated harvest until harvest.

Tomato plants of different varieties are treated with the disclosed composition comprising 1-MCP as shown in Example 5, infra.

Example 5A shows an increase in tomato yield by treating processing tomato plant of variety AB2 with a composition comprising 1-MCP at one or more of the following times: (i) during the period from initiation of the first bloom period (bloom1) to seven days after the initiation of the first bloom period (bloom2) and (ii) one or more times during the period from 28 days before anticipated harvest until harvest (day28). Furthermore, Example 5A shows that Brix yield (i.e., soluble solids, total soluble solids, soluble solids content), which is a measurement of tomato quality, is enhanced by treating processing tomato plant of variety AB2 with a composition comprising 1-MCP. Thus, the disclosed methods not only increase crop yield of the tomato plants, but also enhance quality of tomatoes obtained from such tomato plants.

Example 5B shows that an increase in tomato yield (either based on weight of tomato crops/planted area, or numbers of tomato crops/planted area) is achieved by contacting processing tomato plant of variety 410 with a composition comprising 1-MCP, while the tomato plants are at initiation of the first bloom period (bloom1) or at seven days after the initiation of the first bloom period (bloom2). However, the treatment of tomato plants variety 410 at initiation of the first bloom period (bloom1) provides superior improvement in tomato yield, compared to the treatment at seven days after the initiation of the first bloom period (bloom2).

Example 5C shows an increase in tomato yield by treating fresh market tomato plant of variety FL74 with a composition comprising 1-MCP at one or more of the following times: at the initiation of the first bloom period; seven days after the initiation of the first bloom period, 28 days before anticipated harvest, and 14 days before anticipated harvest.

One particular embodiment of present disclosure is directed to methods of treating bell pepper plants.

Bell pepper plants are treated at least one time, with at least one treatment taking place at any time during any reproductive stage. In some embodiments, bell pepper plants are treated at the initiation of the first bloom period.

Among embodiments involving treatment of bell pepper plants, suitable treatment rates include, for example, 5 g/ha or more; or 10 g/ha or more; or 20 g/ha or more. Independently, among embodiments involving treatment of bell pepper plants, suitable treatment rates include, for example, 100 g/ha or less; or 60 g/ha or less; or 30 g/ha or less.

Example 6, infra, shows an increase in bell pepper yield by treating bell pepper plants at the initiation of the first bloom period with a composition comprising 1-MCP at different dosage of 1-MCP. TABLE 5 summarizes the effect of treating bell pepper plant at the initiation of the first bloom period on pepper yield.

TABLE 5

| Treatment Dosage of 1-MCP (g/ha) | Crop Yield (Total Bell peppers/planted area) | % Increase in Crop Yield |
|---|---|---|
| Untreated | 176 | n/a |
| 5 | 292 | 66% |
| 25 | 243 | 38% |

As shown in TABLE 5, a significant increase in crop yield (i.e., total number of bell peppers obtained per planted area) is achieved by treating bell pepper plants at the initiation of the first bloom period with a composition comprising 1-MCP One particular embodiment of present disclosure is directed to methods of treating watermelon plants.

Watermelon plants are treated at least one time, with at least one treatment taking place at any time during any reproductive stage. The timing of treatments of watermelon plants can usefully be described as "DAF"; i.e., days after flowering, which means the number of days after the beginning of flowering. In some embodiments, watermelon plants are treated one or more times at 1 to 14 DAF. In some embodiments, watermelon plants are treated at any one of or at any combination of the following timings: 1 DAF, 7 DAF, and 14 DAF.

The treatment rate may include, for example, 1 g/ha or more; or 2 g/ha or more; or 5 g/ha or more. Independently, among embodiments involving treatment of watermelon plants, suitable treatment rates include, for example, 100 g/ha or less; or 60 g/ha or less; or 30 g/ha or less.

In one particular embodiments, a method of treating watermelon plants comprises contacting watermelon plants one or more time with a composition comprising at least one cyclopropene within 14 days after flowering of watermelon plants.

Example 7, infra, shows an increase in crop yield of watermelon plants (based on total number of marketable watermelons per watermelon plant, as well as total mass of marketable watermelon per planted area) by treating watermelon plants with a composition comprising 1-MCP at different time after the flowering of watermelon plants. TABLE 6 summarizes the effect on crop yield upon treating watermelon plants at different time periods after flowering and at different dosages of 1-MCP.

TABLE 6

| Treatment Dosage of 1-MCP (g/ha) | Treatment Time (no. of days after flowering) | % Increase in Crop Yield based on Numbers. of watermelons/plant | Mass of watermelon/planted area |
|---|---|---|---|
| Untreated | n/a | n/a | n/a |
| 5 | 7 | 13.76 | 4.05 |
| | 14 | 32.11 | 30.86 |
| | 7 and 14 | 28.44 | 25.68 |
| 10 | 7 | 34.86 | 36.49 |
| | 14 | 22.02 | 16.89 |
| | 7 and 14 | 22.02 | 15.77 |
| 25 | 7 | 36.70 | 28.38 |
| | 14 | 30.28 | 28.60 |
| | 7 and 14 | 18.35 | 13.29 |

As shown in TABLE 6, a significant increase in crop yield of watermelon plants, either based on total number of marketable watermelons per plant, or total mass of marketable watermelon per planted area) is achieved by treating watermelon plants one or more time with a composition comprising 1-MCP within 14 days after flowering of watermelon plants One particular embodiment of present disclosure is directed to methods of treating cantaloupe plants.

Cantaloupe plants are treated at least one time, with at least one treatment taking place at any time during any reproductive stage. In some embodiments, cantaloupe plants are treated one or more times in the period from bud initiation to 10 days after blossom opening. In some embodiments, cantaloupe plants are treated after bud initiation but before blossom opening. In some embodiments, cantaloupe plants are treated 10 days after blossom opening.

Suitable treatment rates include, for example, 5 g/ha or more; or 10 g/ha or more; or 20 g/ha or more. Independently, among embodiments involving treatment of cantaloupe plants, suitable treatment rates include, for example, 100 g/ha or less; or 60 g/ha or less; or 30 g/ha or less.

In one particular embodiments, a method of treating cantaloupe plants comprises contacting cantaloupe plants one or more time with a composition comprising at least one cyclopropene after bud initiation but before blossom opening.

Example 8, infra, and TABLE 7 below show a crop yield of cantaloupe plants (based on average first flower set) by treating cantaloupe plants at different development stage of cantaloupe plants with the composition comprising 1-MCP having a dosage of 1-MCP from about 5 g/ha to about 25 g/ha.

TABLE 7

| Development Stage of Cantaloupe Plants at time of Treatment | Average First Flower Set |
|---|---|
| Untreated | 0.137 |
| After Bud Initiation, but Before Blossom Opening | 0.161 |
| 10 Days After Blossom Opening | 0.0247 |

As shown in TABLE 7, an increase in crop yield of cantaloupe plants is achieved by treating cantaloupe plants one or more time with the composition comprising 1-MCP after bud initiation but before blossom opening.

In some embodiments, rice plants are contacted one or more times with the composition of present disclosure during one or more vegetative stage, one or more reproductive stage, one or more ripening stage, or any combination thereof.

In some embodiments, oilseed rape plants (also called rapeseed plants) are contacted one or more times with the composition of present disclosure after at least 10% of the oilseed rape plants have begun to bloom.

In some embodiments, apple trees are contacted one or more times with the composition of present disclosure before harvest to improve crop yield. For example, as shown in Example 9, the Golden Delicious apple trees were treated with a composition comprising 1-MCP one week before harvest at a dosage rate of 375 gram 1-MCP per one hectare. TABLE 8 shows the number of dropped apple fruits per tree at different time period after the treatment. For comparison, the results for the treatment using 1-naphthaleneacetic acid (NAA) at 20 ppm, and aminoethoxyvinylglycine (AVG) at 125 ppm are also reported.

TABLE 8

| No. of Days after Treatment | Numbers of Dropped Apple Fruits per Tree | | | |
|---|---|---|---|---|
| | Untreated | NAA treated | AVG treated | 1-MCP treated |
| 0 | 0 | 0 | 0 | 0 |
| 7 | 18 | 5 | 5 | 4 |
| 62 | 30 | 11 | 11 | 9 |
| 21 | 45 | 20 | 23 | 15 |
| 28 | 115 | 65 | 35 | 20 |
| 35 | 195 | 118 | 45 | 39 |

As shown in TABLE 8, the apple trees treated with a composition comprising 1-MCP show about five times lower in the number of dropped apples per trees compared to untreated apple trees, and thereby provide a significant increase in apple yield. Furthermore, the apple trees treated with a composition comprising 1-MCP provide lower number of dropped apples per trees compared to the apple trees treated with 1-naphthaleneacetic acid (NAA) or aminoethoxyvinylglycine (AVG).

In some embodiments, an improvement in crop yield is evident at the time of harvest, such as, for example, when the improvement is an increase in weights (i.e. mass) or numbers of crops per unit area of land as disclosed in Examples 1-9.

In some embodiments, an improvement in crop yield is observed some time after the crop has been in storage. That is, in some cases, the crop yield is measured as the amount of high-quality crop that is delivered to the retail market after storage.

Some embodiments of the present disclosure involve pre-harvest contacting of crop plants with the disclosed composition to provide crops that can be put in storage after harvest and then come out of storage with higher quality than previously obtainable.

For example, apples sometimes develop an undesirable clear appearance in the flesh of the fruit known as "water core" while still on the apple trees. Water core, when present, can persist during storage after harvest. In some embodiments of the present disclosure, apple trees are contacted with the composition of present disclosure prior to harvest, and the resulting crop of apples has an improved resistance to developing water core. As shown in Example 10, upon treating Scarletspur Delicious apple trees with a composition comprising 1-MCP at a dosage rate of 375 gram 1-MCP per one hectare immediately before harvest timing, a higher percentage of water core-free apples may be achieved.

Similarly, some varieties of apples (such as, for example, Fuji apples) develop undesirable red spots known as "staining" during storage after harvest. In some embodiments of the present disclosure, apple trees are contacted with the composition of present disclosure prior to harvest, and the resulting crop of apples has an improved resistance to developing red spots during storage. As shown in Example 11, Fuji apple trees treated one or two times with a composition comprising 1-MCP at a dosage rate of 211 gram 1-MCP per one hectare prior to harvest, provides a lower percentage of apples with staining compared to the untreated Fuji apple trees.

Also contemplated are embodiments in which the composition of present disclosure is applied to crop plants or seedlings prior to transplanting from one location to another location.

Thus, in other aspect for present disclosure, a method of treating crop plants or seedlings comprises contacting the crop plants or seedlings one or more times with a composition comprising at least one cyclopropenes, and transplanting the crop plants or seedlings from one location to another location. The composition may be a gaseous composition, a liquid composition, or a solid composition.

Plants are subjected to transplant shock when they are transplanted from one location to another location. Transplant shock involves various abiotic environment stresses, such as heat, drought, cold, low or high solar radiation, air pollutants, or water pollutants (high salt, metals, etc.)

Upon treating crop plants or seedlings one or more times with the disclosed composition, fast recovery of the crop plants or seedlings from transplant shock may be achieved. Indications of fast recovery may include, but are not limited to, one or more of following:

a. faster shoot growth, production of green tissue (leaves+stems), and height;
b. faster root growth;
c. less damage on existing leaves (e.g., less yellowing, tip burn);
d. quicker establishment of upright position;
e. less wilting in days following transplantation;
f. greater biomass accumulation;
g. faster time to flowering and reproductive stages; or
h. more fruit set per plant and higher yield.

The methods of present disclosure may provide a transplant shock protection to the treated crop plants against various stresses, including, but not limited to heat, drought, cold, low or high solar radiation, air pollutants, and water pollutants.

The methods of present disclosure may provide a transplant shock protection across all vegetable species, but most importantly in solanaceous (tomato, pepper, eggplant), cucurbits (melon, cucumber), and cruciferous crops (broccoli, cauliflower, cabbage, brussel sprouts).

The methods of present disclosure may provide a transplant shock protection for transplanting crop plants to either greenhouse production environment, field environment, or both.

In some embodiments, the disclosed composition may be applied to plants while the plants are growing in a container, e.g., pots, flats, or portable beds. In some of such embodiments, when treated plants are subsequently transplanted to open ground, the treated plants show enhanced resistance to transplant shock over the untreated plants.

In one embodiment of such aspect, a method of treating crop plants or seedlings comprises contacting seedlings of crop plants one or more times with a composition comprising at least one cyclopropenes, transplanting the treated seedlings from one location to another location; and allowing the transplanted seedlings to grow to maturity.

Suitable treatment may be performed on plants that are planted in a control environment (e.g., seedlings in greenhouse, hotbed, cold frame), in open ground, in one or more containers (such as, for example, a pot, planter, or vase), in confined or raised beds, or in other places.

In further aspect of the present disclosure, a method of treating dicot seedlings comprises contacting dicot seedlings one or more times with a composition comprising at least one cyclopropenes prior to transplanting the dicot seedlings (e.g., from minutes to 7 days prior to transplanting the dicot seedlings). The composition may be a gaseous composition, a liquid composition, or a solid composition.

While there have been reports of using 1-MCP for treating plants, the reports are directed to the immediate effect of 1-MCP on plants wherein plants are treated with 1-MCP at or near their reproductive stage to increase photosynthetic efficiency, reduce cell damage, and lower abortion of reproductive structures (flowers, pods, bolls, kernels). The effect of the treatment is reported to last only a few days and is not a long term effect such as two to three months after the application.

In the methods of present disclosure, upon applying a composition comprising at least one cyclopropenes (e.g., 1-MCP) to dicot seedlings prior to transplanting, a dramatic increase in yield is achieved many weeks or months after the application. Example 12 shows the treatment of tomato seedlings with a composition comprising about 50 ppm of 1-MCP three days before transplanting the seedlings to hot stress conditions in greenhouse. At the end of 21 days after transplanting, the tomato plants grown from the treated tomato seedlings show higher height, numbers of branches and leafs, shoot dry weight, and root dry weight than the tomato plants grown from untreated tomato seedlings. Example 13 shows the treatment of tomato seedlings with a composition comprising about 50 ppm 1-MCP at three days before the seedling are transplanted to a field and grown to maturity. The transplanted tomato plants grown from the treated seedlings provided higher percentage of large-size tomatoes compared to the transplanted tomato plants grown from untreated seedlings. Furthermore, the amount of large-size tomatoes obtained from the transplanted tomato plants grown from the treated seedlings are double the amount obtained from the transplanted tomato plants grown from untreated seedlings. Example 14 shows the treatment of cabbage seedlings with a composition comprising about 50 ppm 1-MCP immediately before the seedling are transplanted to a field and grown to maturity. The transplanted cabbage plants grown from the treated seedlings provide the cabbage crop with higher head weight and at higher mass yield compared to the transplanted cabbage plants grown from untreated seedlings.

Thus, applications of a composition comprising 1-MCP at minutes to 7 days before transplanting dicot seedlings (e.g., tomato, pepper, crucifer, and cucurbit crops) improve the crop yield by 5-70%. The significant increase in yield is largely due to the substantial increase in fruit numbers which are set months after the application of a composition comprising 1-MCP. These results are unexpected in that the effect is a long term effect of significantly higher yields in dicot seedlings that were treated as small seedlings prior to transplantation. This in spite of the dicot seedlings being grown in cells where roots are not damaged prior to transplantation (i.e., little to no seedling damage). These significant effects on crop yield is not observed in rice. Further, the treatment has large effects on fruit numbers, in spite of the fact that the fruit are set months after the 1-MCP treatment.

The disclosed methods of treating dicot seedlings (e.g., vegetable seedlings) one or more time with a composition comprising at least one cyclopropenes (e.g., 1-MCP) prior to transplanting the dicot seedlings help the dicot seedlings overcome transplant shock by recovering from transplant shock faster, flowering earlier, producing more fruits, and therefore resulting in higher yields.

It is to be understood that for purposes of the present specification and claims that the range and ratio limits recited herein can be combined. For example, if ranges of 60 to 120 and 80 to 110 are recited for a particular parameter, then the ranges of 60 to 110 and 80 to 120 are also contemplated. For another example, if minimum values for a particular parameter of 1, 2, and 3 are recited, and if maximum values of 4 and 5 are recited for that parameter, then it is also understood that the following ranges are all contemplated: 1 to 4, 1 to 5, 2 to 4, 2 to 5, 3 to 4, and 3 to 5.

The following examples serve to explain embodiments of the present disclosure in more detail. These examples should not be construed as being exhaustive or exclusive as to the scope of this disclosure

EXAMPLES

The following materials were used:

Powder 1=powder containing 3.8% 1-MCP by weight, available as AFXRD-038 from Rohm and Haas Co.

Powder 2=powder containing 2.0% 1-MCP by weight, available as AFXRD-020 from Rohm and Haas Co.

Adjuvant 1=oil "AF-400," which contains an emulsified spray oil PureSpray Spray Oil 10E (severely hydrotreated mineral oils with added emulsifier) from Petro Canada Co., an AEROSOL™ OT surfactant (sodium dioctyl sulfosuccinate surfactant) from Cytec Industries, and TOMADOL™ surfactant (ethoxylated alcohol surfactant) from Tomah Co.

Adjuvant 2=DYNE-AMIC™ spray oil, available from Helena Chemical.

Example 1: Soybean Plants

To prepare the tested composition, spray tank was filled with approximately two-thirds of the total volume of water required. The amount of Powder 1 or Powder 2 was weighed according to the rate and total volume of spray being prepared. The appropriate amount was calculated to give 1% v/v of total spray volume. Adjuvant 1 was added to the spray tank, which was agitated until the mixture turned milky white. Powder 1 or Powder 2 was added to the spray container, which was then gently (not vigorously) agitated. The remaining water was added, making sure all of the powder was wet and washed off of the sides of the tank (if any had deposited there). The spray tank was then swirled or stirred for at least two minutes (2-5 minutes) to ensure good mixing of the composition. Between 5 and 60 minutes thereafter, soybean plants were sprayed with the composition.

Flat fan nozzles were used to apply the tested composition to soybean plants, producing droplet size of 100 to 500 micrometers. Spray rate of the composition was 500 liter per hectare. Backpack sprayer was used. Spraying was performed before 10:00 am.

Soybean plants were treated with the tested composition when the soybean plants were at one or more of the following growth stages: R2, R3, and R5.5. The results are shown below:

| Number | Dosage of 1-MCP (g/ha) | Development Stage(s) at Time of Application | Yield (kg/ha) | Protein Content (%) |
|---|---|---|---|---|
| 1 | Untreated | | 3607.20 | 36.93 |
| 2 | Adjuvant 1 only | R2, R3, and R5.5 | 3661.56 | 37.02 |
| 3 | 1 | R2 | 3691.44 | 37.88 |
| 4 | 1 | R3 | 3795.48 | 37.89 |
| 5 | 1 | R5.5 | 3659.76 | 38.25 |
| 6 | 1 | R2 and R3 | 3786.48 | 37.85 |
| 7 | 1 | R2 and R5.5 | 3704.04 | 38.45 |
| 8 | 1 | R3 and R5.5 | 3763.80 | 38.75 |
| 9 | 1 | R2, R3, and R5.5 | 3955.68 | 38.4 |
| 10 | 10 | R2 | 3671.64 | 37.67 |
| 11 | 10 | R3 | 3757.68 | 38.64 |

-continued

| Number | Dosage of 1-MCP (g/ha) | Development Stage(s) at Time of Application | Yield (kg/ha) | Protein Content (%) |
|---|---|---|---|---|
| 12 | 10 | R5.5 | 3721.32 | 38.32 |
| 13 | 10 | R2 and R3 | 3872.84 | 38.27 |
| 14 | 10 | R2 and R5.5 | 3817.80 | 38.63 |
| 15 | 10 | R3 and R5.5 | 3791.52 | 38.3 |
| 16 | 10 | R2, R3, and R5.5 | 4119.48 | 37.87 |
| 17 | 30 | R2 | 3702.24 | 38.08 |
| 18 | 30 | R3 | 3747.24 | 38.33 |
| 19 | 30 | R5.5 | 3817.80 | 37.58 |
| 20 | 30 | R2 and R3 | 4118.76 | 36.73 |
| 21 | 30 | R2 and R5.5 | 3844.44 | 38.56 |
| 22 | 30 | R3 and R5.5 | 3946.68 | 37.87 |
| 23 | 30 | R2, R3, and R5.5 | 4347.00 | 37.48 |

Treatment of soybean plants with a composition comprising 1-MCP while the soybean plants were at the reproductive stage of R2 (full bloom), R3 (beginning pod) and/or R5.5 (between beginning seed and full seed) resulted in an increase in soybean crop yield, as well as an improvement in the protein content of the harvested soybean crops.

Example 2: Corn Plants

Corn of hybrid variety FR1064 X LH185 was planted at 72,000 plants per hectare (ha), and treated as described in Example 1. Powder 1 was used. Treatment stage (i.e., developmental stage at which corn plants are treated with the disclosed composition), treatment amounts (grams of 1-MCP per hectare), and results were as follows. The simple measure of yield is reported as metric ton (mT) per hectare. Other measures of yield are also shown. Treatments lead to increase in yield by one or more measures.

| Development Stage(s) at Time of Application | 1-MCP Dosage (g/ha) | Yield (mT/ha) | Kernel wt (mg) | Kernel no.[1] | Protein %[2] | Starch %[2] | Oil %[2] |
|---|---|---|---|---|---|---|---|
| Untreated[3] | 0 | 1.64 | 248 | 444 | 7.8 | 71.7 | 4.6 |
| V12 | 10 | 1.80[4] | 266[4] | 471 | 7.7 | 71.7 | 4.6 |
| V12 | 25 | 1.84[4] | 270[4] | 495[4] | 7.5 | 72.0 | 4.6 |
| VT | 10 | 1.86[4] | 267[4] | 480 | 7.5 | 72.1[4] | 4.5 |
| VT | 25 | 1.87[4] | 277[4] | 451 | 7.7 | 71.7 | 4.6 |
| R3 | 10 | 1.81[4] | 265[4] | 454 | 7.3 | 72.2 | 4.6 |
| R3 | 25 | 1.82[4] | 265[4] | 471 | 7.6 | 72.1 | 4.7 |
| V12, VT | 10 | 1.82[4] | 263[4] | 459 | 7.6 | 71.9 | 4.5 |
| VT, R3 | 10 | 1.72 | 271[4] | 437 | 7.7 | 71.6 | 4.8[4] |
| V12, VT, R3 | 10 | 1.70 | 259 | 464 | 7.2[4] | 72.4[4] | 4.6 |

Notes:
[1]number of kernels per plant
[2]weight of protein (or starch or oil) as a percent based on the weight of the kernels
[3]untreated control. No 1-MCP was used
[4]statistically distinct from the result obtained in the untreated corn plants

Example 3: Cotton Plants

Using methods similar to those of Example 1, cotton plants were also tested. Each treated group of cotton plants was treated either two or three times, as follows:

| Treatment Type | Time of First Treatment | Time of Second Treatment | Time of Third Treatment |
|---|---|---|---|
| PHS 2 | Soon after appearance of pinhead squares | 14 days after first treatment | none |
| PHS 3 | Soon after appearance of pinhead squares | 14 days after first treatment | 28 days after first treatment |
| EB 2 | Soon after appearance of early bloom | 14 days after first treatment | none |
| EB 3 | Soon after appearance of early bloom | 14 days after first treatment | 28 days after first treatment |

The crop yield was assessed as the weight of lint per hectare. Treatment types, treatment amounts (grams of 1-MCP per hectare), and results were as follows. Many of the treatments lead to improvements in the yield of lint.

| Dosage of 1-MCP (g/ha) | Treatment Type | Lint Yield (kg/ha) |
|---|---|---|
| 250 | PHS 2 | 230.6 |
| 250 | PHS 3 | 231.8 |
| 250 | EB 2 | 245.3 |
| 250 | EB 3 | 250.2 |
| 500 | PHS 2 | 257.6 |
| 500 | PHS 3 | 262.0 |
| 500 | EB 2 | 234.2 |
| 500 | EB 3 | 261.3 |
| 1250 | PHS 2 | 253.9 |
| 1250 | PHS 3 | 241.4 |
| 1250 | EB 2 | 235.0 |
| 1250 | EB 3 | 260.7 |
| 0 | Untreated | 228.0 |
| 0 | Adjuvant 1 only | 245.1 |

Example 4: Wheat Plants

Using methods similar to those of Example 1, wheat plants were sprayed at stage F10.5. Frost damage was assessed by examining the portion of the seed head damaged, and reported as the percentage of barren husks. Damage from fusarium disease was assessed as a percentage of seed heads damaged by the disease organism. The following table shows that the treated wheat plants showed higher yield, lower frost damage, and lower disease damage.

| Dosage of 1-MCP (g/ha) | Crop Yield (kg dry weight/ha) | Frost Damage (%) | Disease Damage (%) |
|---|---|---|---|
| 0 | 3890 | 21 | 6 |
| 10 | 4458 | 6 | 0.5 |
| 25 | 4522 | 3 | 3 |

Example 5: Tomato Plants

To prepare the tested composition, a spray tank was filled with approximately two-thirds of the total volume of water required. The amount of Powder 1 or Powder 2 was weighed according to the intended treatment rate and total volume of spray being prepared. The appropriate amount was calculated to give 0.38% v/v of total spray volume. Adjuvant 2 was added to the spray tank, which was agitated until the mixture turned milky white. Powder 1 or Powder 2 was added to the spray container, which was then gently (not vigorously) agitated. The remaining water was added, making sure all of the powder was wet and washed off of the sides of the tank (if any had deposited there). The spray tank was then swirled or stirred for 2 to 5 minutes to ensure good mixing of the composition Between 5 and 60 minutes thereafter, tomato plants were sprayed with the composition.

Flat fan nozzles were used to apply the composition to tomato plants, producing droplet size of 100 to 500 micrometers. Spray rate of the composition was 187 to 373 liter per hectare (20 to 40 gallons per acre). Carbon dioxide-powered backpack sprayer was used. Spraying was performed before 10:00 am.

The tomato plants were treated with the composition while the tomato plants at the following time:

bloom1=initiation of the first bloom period
bloom2=7 days after initiation of the first bloom period
day28=28 days before anticipated harvest
day21=21 days before anticipated harvest
day14=14 days before anticipated harvest A. Tomato Plants of Variety AB2

Tomato plants of variety AB2 were grown in Gainesville, FL. Brix is soluble solids (also called total soluble solids or soluble solids content) and is a measurement of tomato quality. Treatment was conducted by spraying tomato plants with the tested composition at the 1-MCP dosage of 25 g/ha (9.4 oz/acre).

Results were as shown in the following tables, wherein the fruit yield is reported as mT/ha (tons/acre), the Brix yield is reported as solids weight per unit land area, i.e., mT/ha (tons/acre), and the delay in harvest is reported as % mature green.

Trial 1

| Treatment Timing | Fruit Yield | Brix Yield | Delay |
|---|---|---|---|
| bloom1 | 243 (44) | 12.1 (2.18) | 10 |
| bloom1 and bloom2 | 227 (41) | 12.0 (2.17) | 11 |
| day28 | 221 (40) | 11.6 (2.10) | 9 |
| Untreated | 199 (36) | 10.5 (1.89) | 8 |

Trial 2

| Treatment | Fruit Yield | Brix Yield | Delay |
|---|---|---|---|
| bloom1 | 194 (35) | 11.0 (1.99) | 4 |
| bloom1 and bloom2 | 205 (37) | 11.5 (2.08) | 3 |
| day28 | 183 (33) | 10.9 (1.97) | 4 |
| Untreated | 177 (32) | 9.4 (1.70) | 5 |

Trial 3

| Treatment | Fruit Yield | Brix Yield | Delay |
|---|---|---|---|
| bloom1 and bloom2 | 111 (20) | 6.4 (1.15) | 13 |
| day28 | 116 (21) | 6.3 (1.14) | 17 |
| Untreated | 105 (19) | 5.8 (1.04) | 15 |

Trial 4

| Treatment | Fruit Yield | Brix Yield | Delay |
|---|---|---|---|
| bloom1 and bloom2 | 304 (55) | 14.9 (2.7) | 5 |
| Untreated | 288 (52) | 14.4 (2.6) | 4 |

Tomato plants of variety AB2 that were treated with a composition comprising 1-MCP showed improvement in fruit yield as well as Brix yield, compared to the untreated tomato plants of variety AB2.

B. Tomato Plants of Variety 410

Tomato plants of variety 410 were grown and treated as described above. Results were as shown in the following tables, wherein the fruit yields are reported as Fruit Mass in mT/ha (tons/acre) unit, and as Fruit Number in thousands of fruit per hectare (thousands per acre) unit.

Trial 5

| Treatment | Fruit Mass | Fruit Number |
|---|---|---|
| bloom1 | 354 (64) | 2245 (909) |
| bloom2 | 376 (68) | 2406 (974) |
| Untreated | 327 (59) | 2062 (835) |

Tomato plants of variety 410 that were treated with a composition comprising 1-MCP showed improvement in tomato yield (based on either the amounts of tomato mass/acre or the numbers of tomatoes/acre), compared to the untreated tomato plants of variety 410.

C. Tomato Plants of Variety FL 47

Tomato plants of variety FL 47 were grown in Florida and were treated as described above. Yield is reported as mT/hectare (Cwt/acre, i.e., number of hundred-pound groups per acre) Results were as follows:

Trial 6

| Treatment | Yield |
|---|---|
| bloom1 | 27.0 (241) |
| bloom2 | 21.5 (192) |
| bloom1 and bloom2 | 23.3 (208) |
| Untreated | 19.4 (173) |

Trial 7

| Treatment | Yield |
|---|---|
| bloom1 | 18.3 (163) |
| bloom2 | 18.6 (166) |
| bloom1 and bloom2 | 17.2 (154) |
| Untreated | 15.8 (141) |

Trial 8

| Treatment | Yield |
|---|---|
| day21 | 24.2 (216) |
| day14 | 20.4 (182) |
| day21 and day14 | 22.3 (199) |
| Untreated | 19.4 (173) |

Tomato plants of variety FL47 that were treated with a composition comprising 1-MCP showed improvement in tomato yield, compared to the untreated tomato plants of variety FL47.

Example 6: Bell Pepper Plants

Bell Pepper plants of Lady Bell variety was grown in Fostoria, Ohio on a small plot and treated with the tested liquid compositions, as described in Example 5, with one treatment at the initiation of the first bloom period. Treatment rates are reported as g/ha (oz/acre). Results are reported as Total Fruit (total number of bell peppers grown on the entire plot), Fruits per Plant (average number of bell peppers per one plant), and Total Plants (total number of plants grown on the entire plot). "NS" means that the liquid composition contains no surfactant. Results were as follows:

| Dosage of 1-MCP in g/ha (oz/acre) | Total Fruits | Fruits per Plant | Total Plants |
|---|---|---|---|
| Untreated | 176 | 6.1 | 16 |
| 5 (1.9) | 292 | 10.1 | 23 |
| 25 (9.4) | 243 | 8.4 | 22 |
| 25 (9.4)NS | 231 | 8 | 22 |

Bell pepper plants that were treated with a composition comprising 1-MCP provided higher numbers of bell peppers per planting plot and per plant, compared to the untreated bell pepper plants. Thus, an increase in crop yield of bell pepper plants was achieved by contacting bell pepper plants with a composition comprising 1-MCP increased at the initiation of the first bloom period of bell paper plants.

Example 7: Watermelon

Watermelon (variety triploid cv. SS 7187) plants were treated as described in Example 5. Treatment rates are reported in grams 1-MCP per hectare. Timing is reported as DAF (days after flowering). A marketable melon is a harvested melon with mass of 4.54 kg or greater. A cull is a harvested melon with mass less than 4.54 kg or an unharvested melon that had diameter greater than 5 cm. The following results are reported:

- Num25=number of fruit of diameter greater than 5 cm per plant, assessed before harvest, at 25 DAF, also known as "fruit set"
- NumTot=Harvested and Unharvested Fruits, 42-56 Days, with diameter greater than 5 cm
- NumMark=number of marketable melons per plant
- NumCull=number of culls per plant
- Size=average size of fruit, in kg
- Yield=mass of marketable melons, in metric tons per hectare

| Treatment Rate | Timing (no. days after flowering) | Num25 | NumMark | NumCulls | Yield | Size |
|---|---|---|---|---|---|---|
| Untreated | — | 1.25 | 1.09 | 0.78 | 44.4 | 7.46 |
| 5 | 7 | 1.25 | 1.24 | 0.64 | 46.2 | 6.83 |
| 5 | 14 | 1.83 | 1.44 | 0.58 | 58.1 | 7.44 |
| 5 | 7 and 14 | 1.58 | 1.40 | 0.71 | 55.8 | 7.26 |
| 10 | 7 | 1.17 | 1.47 | 0.71 | 60.6 | 7.56 |
| 10 | 14 | 1.42 | 1.33 | 0.64 | 51.9 | 7.09 |
| 10 | 7 and 14 | 1.67 | 1.33 | 0.78 | 51.4 | 7.10 |

-continued

| Treatment Rate | Timing (no. days after flowering) | Num25 | NumMark | NumCulls | Yield | Size |
|---|---|---|---|---|---|---|
| 25 | 7 | 1.58 | 1.49 | 0.58 | 57.0 | 7.08 |
| 25 | 14 | 1.75 | 1.42 | 0.58 | 57.1 | 7.41 |
| 25 | 7 and 14 | 1.92 | 1.29 | 0.60 | 50.3 | 7.15 |

As shown in the table above, the watermelon plants treated with a composition at 1-MCP dosage rate of 25 g/ha resulted in a significant increase in fruit set over the untreated watermelon plants. The treated watermelon plants also showed a significant increase in the number of marketable fruit over the untreated watermelon plants. Furthermore, the treated watermelon plants showed a significant increase in yield over the untreated watermelon plants. Differences in fruit size between the treated watermelon plants and the untreated watermelon plants were not significant.

Example 8: Cantaloupe Plants

Cantaloupe plants were treated as described in Example 5. Timing of treatment was before blossom opening or ten days after blossom opening. The average first flower set was measured. Results were as follows:

| Development Stage of Cantaloupe plants at the Time of Treatment | Average First Flower Set |
|---|---|
| Untreated | 0.137 |
| Before blossom opening | 0.161 |
| 10 days after blossom opening | 0.0247 |

As shown in the table above, the cantaloupe plants treated with a composition comprising 1-MCP before blossom opening provided improved average first flower set over the untreated cantaloupe plants.

Example 9: Golden Delicious Apple Trees

Golden Delicious apple trees were sprayed with a composition comprising 1-MCP one week before they were harvested using methods similar to those described in Example 1. The composition comprising 1-MCP was prepared from Powder 1 and tested at a dosage rate of 375 gram 1-MCP per one hectare. For comparison, 1-Naphthaleneacetic acid (NAA) at 20 ppm, and aminoethoxyvinylglycine (AVG) at 125 ppm were also tested.

The treated apples were left on the trees to observe postharvest drop. Numbers of dropped apple fruits per tree were determined after different time period after the treatment as shown in the following table.

| No. Days | Numbers of Dropped Fruit per Tree | | | |
|---|---|---|---|---|
| after Treatment | Untreated | NAA treated | AVG treated | Powder 1 treated |
| 0 | 0 | 0 | 0 | 0 |
| 7 | 18 | 5 | 5 | 4 |
| 62 | 30 | 11 | 11 | 9 |
| 21 | 45 | 20 | 23 | 15 |

-continued

| No. Days | Numbers of Dropped Fruit per Tree | | | |
|---|---|---|---|---|
| after Treatment | Untreated | NAA treated | AVG treated | Powder 1 treated |
| 28 | 115 | 65 | 35 | 20 |
| 35 | 195 | 118 | 45 | 39 |

As shown in the table above, apple trees treated with a composition comprising 1-MCP showed the least amount of dropped apple fruit per tree and thereby the highest crop yield.

Example 10: Scarletspur Delicious Apple Trees

Scarletspur Delicious apple trees were sprayed with a composition comprising 1-MCP immediately before commercial harvest timing using methods similar to those described in Example 1. The composition comprising 1-MCP was prepared from Powder 1 and tested at a dosage rate of 375 gram 1-MCP per one hectare.

The harvested apples were evaluated for the presence of water core. The following table shows the percentage of apples (based on the number of apples in storage) that showed no water core as a function of days after harvest. The treated apples showed a comparable or higher percentage of water core-free apples.

| | % Apples in the Storage that are free of Water Core | |
|---|---|---|
| Days After Harvest | Untreated Apple Trees | Apple Tree Treated with 1-MCP |
| 4 | 98 | 95 |
| 8 | 98 | 98 |
| 12 | 82 | 98 |
| 15 | 70 | 98 |
| 19 | 66 | 95 |
| 24 | 40 | 98 |
| 29 | 20 | 98 |
| 34 | 10 | 42 |

Example 11: Fuji Apples Trees

Fuji apple trees were sprayed were sprayed with a composition comprising about 250 ppm of 1-MCP, either one or two times, prior to harvest using methods similar to those described in Example 1. Each spraying provided a dosage of 1-MCP of approximately 211 g/ha (520 g/acre). After harvesting and storage, the apples were inspected for staining. The percent of apples that showed staining was as follows:

| Treatment of the Apple Trees | % Apples in Storage with Appearance of Staining |
|---|---|
| Untreated | 12 |
| 1 spray application | 8.5 |
| 2 spray applications | 3 |

As shown in the table above, the apple trees treated with a composition comprising 1-MCP, either one or two times, provided lower amount of apple fruits with staining compared to the untreated apple trees.

Example 12: Tomato Plants Transplanted to Heat Stress Environment in Greenhouse Tomato seedlings were grown under optimal conditions until 4-6 inches in height. A composition comprising about 50 ppm of 1-MCP was applied to the tomato seedling. At three days after the application, tomato seedlings were transplanted and moved into hot stress conditions in greenhouse where they were grown for 21 more days. At the end of 21 days, various variable of the tomato plants grown from the treated tomato seedlings were measured and compared to those of the tomato plants grown from the untreated tomato seedlings. The percentage increase in different variables of the tomato plants grown from the treated tomato seedlings over the tomato plants grown the untreated tomato seedlings as shown in the table below.

| Variable | % 1-MCP Increase |
|---|---|
| Height (cm) | 24% |
| Numbers of Branches | 23% |
| Numbers of Leafs | 10% |
| Shoot Dry Weight | 59% |
| Root Dry Weight | 54% |

At the end of 21 days after transplanting to heat stress environment in greenhouse, the tomato plants grown from the treated tomato seedling showed higher height, numbers of braches and leaf, shoot dry weight, and root dry weight over the tomato plants grown the untreated tomato seedlings.

Example 13: Tomato Plants Transplanted to Field Environment

Tomato seedlings were grown under normal production plant house conditions until 4-6 inches tall. A composition comprising about 50 ppm of 1-MCP was applied to the tomato seedling. At three days after the application, the seedlings were transplanted into field production facility in Florida and grown to maturity. Tomatoes were harvested using standard commercial hand picking practices for fresh tomatoes. The table below showed that the transplanted tomato plants grown from the treated seedlings provided higher percentage of large-size tomatoes compared to the transplanted tomato plants grown from the untreated seedlings. Furthermore, the amount of large-size tomatoes obtained from the transplanted tomato plants grown from the treated seedlings were double the amount obtained from the transplanted tomato plants grown from the untreated seedlings.

| | Numbers of Tomatoes Produced for Transplanted Tomato Seedlings (percentage) | |
|---|---|---|
| Values | Treatment with 1-MCP | Untreated |
| Large | 16,453 (55%) | 8,077 (48%) |
| Medium | 10,305 (34%) | 5,918 (35%) |
| Small | 3,350 (11%) | 2,882 (17%) |

Example 14: Cabbage Plants Transplanted to Field Environment

Cabbage seedlings were grown under normal plant house production practices until ready to transplant to field. A composition comprising about 50 ppm of 1-MCP was applied to the tomato seedlings. Immediately after the application, the seedlings were transplanted into the field trial in Florida and grown to maturity. Cabbage were harvested using standard commercial hand picking practices. The average head weight of cabbage (lb) and the total weight of cabbage obtained per acre were reported below.

| | Avg. Head Weight (lbs) | Total Lb/A |
|---|---|---|
| Treatment with 1-MCP | 16,453 | 8,077 |
| Untreated | 10,305 | 5,918 |
| % Increase by 1-MCP Treatment | 50% | 50% |

As shown in the table above, the transplanted cabbage plants grown from the treated seedlings provided the cabbage crop with higher head weight and at higher mass yield compared to the transplanted cabbage plants grown from the untreated seedlings.

We claim:

1. A method of improving yield of a tomato plant, said method comprising a step of contacting tomato seedlings with a composition comprising 1-methylcyclopropene (1-MCP) at 3 days prior to transplanting the tomato seedlings from one location to another location, wherein the contacting provides an increase in yield of tomato plants or tomato plant parts produced by the tomato seedlings as compared to untreated tomato plants or tomato plant parts.

2. The method of claim 1, wherein the composition is a liquid composition.

3. The method of claim 1, wherein the composition is a gaseous composition.

4. The method of claim 1, wherein the composition comprises about 50 ppm of 1-MCP.

5. The method of claim 1, wherein increasing the yield of the tomato plants or tomato plant parts comprises improvements selected from the group consisting of a greater number of useful plants or plant parts, a higher weight of plants or plant parts, a larger number of useful plants or plant parts meet the minimum criteria of acceptable quality, and combinations thereof.

6. The method of claim 1, wherein the composition further comprises at least one molecular encapsulating agent.

7. The method of claim 1, wherein the composition further comprises at least one metal-complexing agent.

8. A method of improving yield of a cabbage plant, said method comprising a step of contacting cabbage seedlings with a composition comprising 1-methylcyclopropene (1-MCP) immediately prior to transplanting the cabbage seedlings from one location to another location, wherein the contacting provides an increase in yield of cabbage plants or cabbage plant parts produced by the cabbage seedlings as compared to untreated cabbage plants or cabbage plant parts.

9. The method of claim 8, wherein the composition is a liquid composition.

10. The method of claim 8, wherein the composition is a gaseous composition.

11. The method of claim 8, wherein the composition comprises about 50 ppm of 1-MCP.

12. The method of claim 8, wherein increasing the yield of the cabbage plants or cabbage plant parts comprises improvements selected from the group consisting of a greater number of useful plants or plant parts, a higher weight of plants or plant parts, a larger number of useful plants or plant parts meet the minimum criteria of acceptable quality, and combinations thereof.

13. The method of claim 8, wherein the composition further comprises at least one molecular encapsulating agent.

14. The method of claim 8, wherein the composition further comprises at least one metal-complexing agent.

* * * * *